United States Patent
Kato et al.

(10) Patent No.: US 6,180,027 B1
(45) Date of Patent: *Jan. 30, 2001

(54) BISALKENYL DERIVATIVES, LIQUID CRYSTALLINE COMPOUNDS AND LIQUID CRYSTAL COMPOSITIONS

(75) Inventors: Takashi Kato; Shuichi Matsui; Kazutoshi Miyazawa; Yasuko Sekiguchi; Etsuo Nakagawa, all of Chiba (JP)

(73) Assignee: Chisso Corporation, Osaka (JP)

( * ) Notice: Under 35 U.S.C. 154(b), the term of this patent shall be extended for 0 days.

This patent is subject to a terminal disclaimer.

(21) Appl. No.: 09/101,990
(22) PCT Filed: Mar. 6, 1997
(86) PCT No.: PCT/JP97/00700
 § 371 Date: Jul. 22, 1998
 § 102(e) Date: Jul. 22, 1998
(87) PCT Pub. No.: WO97/34855
 PCT Pub. Date: Sep. 25, 1997

(30) Foreign Application Priority Data

Mar. 18, 1996 (JP) .................................................. 8-90585

(51) Int. Cl.$^7$ .......................... C09K 19/30; C09K 19/12; C09K 19/34; C09K 19/02
(52) U.S. Cl. ............................... 252/299.63; 252/299.61; 252/299.66; 349/182
(58) Field of Search ..................... 252/299.63, 299.66, 252/299.61; 349/182

(56) References Cited

U.S. PATENT DOCUMENTS

| | | | | |
|---|---|---|---|---|
| 5,102,578 | * | 4/1992 | Buchecker et al. | 252/299.63 |
| 5,183,587 | * | 2/1993 | Kitano et al. | 252/299.63 |
| 5,328,642 | * | 7/1994 | Rieger et al. | 252/299.63 |
| 5,364,556 | * | 11/1994 | Schadt et al. | 252/299.01 |
| 5,399,292 | * | 3/1995 | Buchecker et al. | 252/299.63 |
| 5,403,512 | * | 4/1995 | Bartmann et al. | 252/299.01 |
| 5,653,911 | * | 8/1997 | Kondo et al. | 252/299.01 |
| 5,658,489 | * | 8/1997 | Higashi et al. | 252/299.01 |
| 5,723,682 | * | 3/1998 | Poetsch et al. | 568/655 |
| 5,730,901 | * | 3/1998 | Shimizu et al. | 252/299.61 |
| 5,776,367 | * | 7/1998 | Matsui et al. | 252/299.63 |
| 5,792,387 | * | 8/1998 | Hachiya et al. | 252/299.6 |
| 5,868,961 | * | 2/1999 | Shimizu et al. | 252/299.61 |
| 5,888,423 | * | 3/1999 | Buchecker et al. | 252/299.63 |
| 5,989,452 | * | 11/1999 | Kato et al. | 252/299.63 |

FOREIGN PATENT DOCUMENTS

| | | |
|---|---|---|
| 4426799 | 2/1995 | (DE) . |
| 0168683 | 1/1986 | (EP) . |
| 0325796 | 8/1989 | (EP) . |
| WO92/21734 | 12/1992 | (WO) . |
| WO93/07234 | 4/1993 | (WO) . |
| WO95/30723 | 11/1995 | (WO) . |

\* cited by examiner

Primary Examiner—C. H. Kelly
(74) Attorney, Agent, or Firm—Wenderoth, Lind & Ponack, L.L.P.

(57) ABSTRACT

Liquid crystalline compounds expressed by the following formula (1), liquid crystal compositions thereof obtained by combination with specified liquid crystal compounds, and liquid crystal display devices using them,

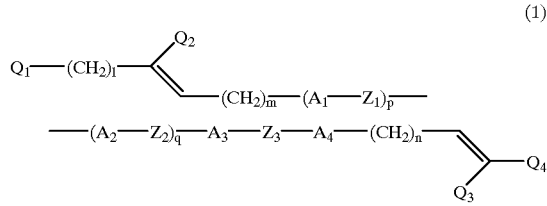

(1)

wherein, $A_1$, $A_2$, $A_3$ and $A_4$ denote each independently trans-1,4-cyclohexylene group etc.; $Z_1$, $Z_2$ and $Z_3$ denote each independently —$(CH_2)_2$— etc.; $Q_1$ and $Q_2$ denote each independently H, F, Cl or Br; $Q_3$ and $Q_4$ denote each independently F, Cl or Br; l, m and n denote each independently an integer of from 0 to 5; and p and q denote each independently an integer of 0 or 1.

17 Claims, No Drawings

BISALKENYL DERIVATIVES, LIQUID CRYSTALLINE COMPOUNDS AND LIQUID CRYSTAL COMPOSITIONS

TECHNICAL FIELD

The present invention relates to liquid crystalline compounds and liquid crystal compositions, in more detail novel liquid crystalline compounds having an alkenyl group optionally substituted by halogen and an alkenyl group substituted by halogen simultaneously at both terminals of compounds, liquid crystal compositions containing them, as well as liquid crystal display devices constituted by using the said liquid crystal ecompositions.

BACKGROUND ART

There have been many display devices which utilizing a refractive anisotropy and a dielectric anisotropy, characteristics of liquid crystalline compounds. Those display devices are used widely in watches, electronic computers, word processsors, television sets etc., demands of which have been increased year by year. Liquid crystal phase is positioned between solid phase and liquid phase, and liquid crystal phase is classified roughly into nematic phase, smectic phase, and cholesteric phase, and among them, display devicesutilizing nematic phase are most widely used.

Furthermore, as display methods applied for liquid crystal displays, there are present TN (twist nematic) type, DS (dinamic scattering) type, guest-host type and DAP type etc. concerning to their electric optical effects. In particular, colorization of liquid crystal display has been recently more progressed, wherein the main currents are a thin film transistor (TFT) method and a super twist nematic (STN) method concerning to TN type, and these display devices are mass-produced.

Although a number of liquid crystalline compounds including those in study are known, there is not present any substance which is enclosed and used in display devices as a single liquid crystalline substance. The reasons thereof is that there has not been found any substance to satisfy the following conditions as a single substance: namely, that liquid crystalline compounds to be expected as materials of display devices are desired to show a liquid crystal phase within a wide temperature range as possible in nature centering around the room temperature, which is most often used for display devices, that the compounds should be sufficiently stable against environmental factors to be used, and that the compounds should have physical properties sufficient for driving display devices.

Thus, compositions having such characteristics are prepared and used practically by mixing several liquid crystalline compounds or non-liquid crystalline compounds. These liquid crystal compositions are required to be stable against moisture, light, heat, and air etc. which are generally present in the used environment. In addition, stabilities against electric field and electromagnetic radiation are necessary and also the liquid crystalline compounds mixed are required to be chemically stable each other in the used environment.

Furthermore, liquid crystal compositions are necessary to have suitable values of physical properties such as a refractive anisotropy value ($\Delta n$), a dielectric anisotropy value ($\Delta \epsilon$), a viscosity ($\eta$), a conductivity and an elastic constant ratio $K_{33}/K_{11}$ ($K_{33}$: bend constant, $K_{11}$: splay elastic constant) etc. according to display methods and device forms. Furthermore, it is important that each components in liquid crystal compositions have good solubilities mutually.

Among these physical property values, particularly a wide liquid crystal phase temperature range, a low viscosity and a high elastic constant ratio $K_{33}/K_{11}$ are required for liquid crystal compounds to be used in a STN type display method. Recently, environments in which display devices being used are divesified so that materials having a wide liquid crystal phase temperature range are necessary from requirements caused by those environments, and a low viscosity is a necessary and indispensable characteristic for attaining a high speed response, and a high elastic constant ratio $K_{33}/K_{11}$ makes a change in a transmittance sharply in vicinity of a threshold voltage and also makes display devices with a high contrast possible.

In general, compounds having (an) alkenyl group(s) are known to show low viscosities. However, when comparing compounds having (an) alkyl group(s) and compounds having (an) alkenyl group (s), compounds having (an) alkenyl group (s) have such tendencies that smectic properties are decreased but liquid crystal phase temperature ranges are also decreased.

Absolutely, from comparison of compounds (a-1) to (c-2) described in V. Vill, Landort-Velunstein, in bicyclohexyl derivatives (a-1) and (a-2), the clearing point of (a-2) having (an) alkenyl group(s) is about 1° C. higher than (a-1) having (an) alkyl group(s), whereas the melting point of the former is about 23° C. higher than the latter. Therefore, the liquid crystal phase temperature range is decreased by about 22° C. The increasing tendencies of the clearing point and theme lting point are found by comparison of cyclohexylphenyl derivatives (b-1) and (b-2), wherein the liquid crystal phase temperature range is decreased by about 10° C.

Furthermore, in biphenyl derivatives (c-1) and (c-2), liquid crystal phase temperature ranges are decreased by about 37° C. owing to decrease in the clearing point and increase in the melting point. In both cases, the liquid crystal phase temperature ranges are eminently decreased by substituting an alkyl group with an alkenyl group.

Furthermore, as to compounds showing a high elastic constant ratio $K_{33}/K_{11}$, there have been already known compounds having (an) alkenyl group(s) in side chains such as compound (d) described in Toku-Ko-Hei 4-30382 or compound (e) described in Toku-Ko-Hei 7-2653. These compounds have however poor appearances of liquid crystal phases, and temperature ranges thereof are very narrow even if appearances are obtained. Thus, in the case that they are used as components of liquid crystal compositions, deposition of crystals or appearance of smectic phase may be confirmed at a lower temperature range so that solubility at a lower temperature cannot be said good.

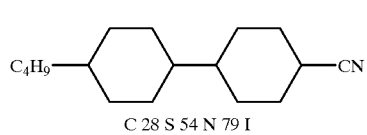

(a-1)

C 28 S 54 N 79 I

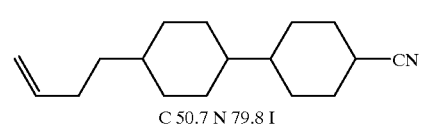

(a-2)

C 50.7 N 79.8 I

-continued

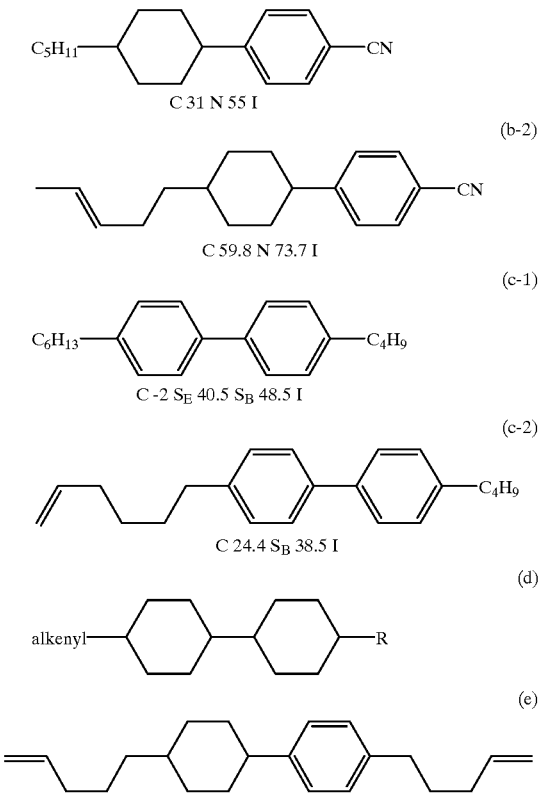

Problems to be Solved by the Invention

An object of the invention is to propose liquid crystalline compounds, liquid crystal compositions containing them and liquid crystal display devices constituted by using the said liquid crystal compositions, wherein a liquid crystal phase temperature range being particularly wide, a viscosity being low, an elastic constant ratio $K_{33}/K_{11}$ being high and a solubility at a lower temperature being improved, in order to solve problems of conventional methods.

Disclosure of Invention

Inventions to be claimed in the present application are as follows.

(1) A liquid crystalline compound expressed by the general formula (1)

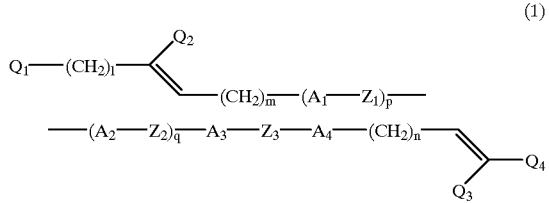

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —$(CH_2)_2$—, —$(CH_2)_4$—, —CH=CH—, —C≡C—, —COO—, —OCO—, —$CH_2O$—, —$OCH_2$—, —CF=CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1.

(2) A liquid crystalline compound according to the above-mentioned (1), wherein p, q and n are 0; $Q_3$ and $Q_4$ are F; $Z_3$ is a covalent bond; and $A_3$ and $A_4$ are trans-1,4-cyclohexylene groups in the general formula (1).

(3) A liquid crystalline compound according to above-mentioned (1), wherein p and q are 0; $Q_3$ and $Q_4$ are F; $Z_3$ is a covalent bond; and $A_3$ and $A_4$ are trans-1,4-cyclohexylene groups in the general formula (1).

(4) A liquid crystalline compound according to above-mentioned (1), wherein p and n are 0; q is 1; $Q_3$ and $Q_4$ are F; $Z_2$ and $Z_3$ are covalent bonds; and $A_2$, $A_3$ and $A_4$ are trans-1,4-cyclohexylene groups in the general formula (1).

(5) A liquid crystalline compound according to above-mentioned (1), wherein p is 0; q is 1; $Q_3$ and $Q_4$ are F; $Z_2$ and $Z_3$ are covalent bonds; and $A_2$, $A_3$ and $A_4$ are trans-1,4-cyclohexylene groups in the general formula (1).

(6) A liquid crystalline compound according to above-mentioned (1), wherein p and n are 0; q is 1; $Q_3$ and $Q_4$ are F; $Z_2$ and $Z_3$ are covalent bonds; $A_2$ is 1, 4-phenylene group; and $A_3$ and $A_4$ are trans-1,4-cyclohexylene groups in the general formula (1).

(7) A liquid crystalline compound according to above-mentioned (1), wherein p is 0; q is 1; $Q_3$ and $Q_4$ are F; $Z_2$ and $Z_3$ are covalent bonds; $A_2$ is 1, 4-phenylene group; and $A_3$ and $A_4$ are trans-1,4-cyclohexylene groups in the general formula (1).

(8) A liquid crystalline compound according to above-mentioned (1), wherein p and n are 0; q is 1; $Q_3$ and $Q_4$ are F; $Z_2$ and $Z_3$ are covalent bonds; $A_2$ and $A_3$ are 1, 4-phenylene groups, and $A_4$ is trans-1,4-cyclohexylene group in the general formula (1).

(9) A liquid crystalline compound according to above-mentioned (1), wherein p is 0; q is 1; $Q_3$ and $Q_4$ are F; $Z_2$ and $Z_3$ are covalent bonds; $A_2$ and $A_3$ are 1, 4-phenylene groups; and $A_4$ is trans-1,4-cyclohexylene group in the general formula (1).

(10) A liquid crystalline compound according to above-mentioned (1), wherein p and q are 1; n is 0; $Q_3$ and $Q_4$ are F; $Z_1$, $Z_2$ and $Z_3$ are covalent bonds; $A_1$ and $A_4$ are trans-1,4-cyclohexylene groups; and $A_2$ and $A_3$ are 1,4-phenylene groups in the general formula (1).

(11) A liquid crystalline compound according to above-mentioned (1), wherein p and q are 1; $Q_3$ and $Q_4$ are F; $Z_1$, $Z_2$ and $Z_3$ are covalent bonds; $A_1$ and $A_4$ are trans-1,4-cyclohexylene groups, and $A_2$ and $A_3$ are 1, 4-phenylene groups in the general formula (1)

(12) A liquid crystal composition consisting of two or more than two components and a display device using the said composition, wherein at least one liquid compound(s) according to any of above-mentioned (1) to (11) is (are) contained.

(13) A liquid crystal composition characterized in that at least one liquid crystalline compound(s) expressed by the general formula (1)

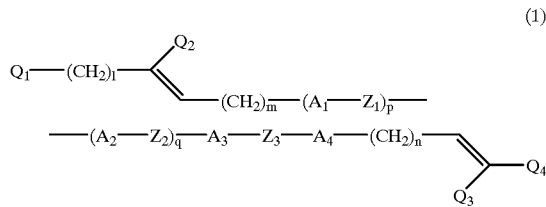

(1)

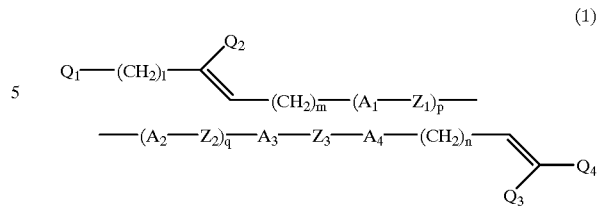

(1)

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —$(CH_2)_2$—, —$(CH_2)_4$—, —CH=CH—, —C≡C—, —COO—, —OCO—, —$CH_2O$—, —$OCH_2$—, —CF=CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, is (are) contained as the first component, and that at least one compound(s) selected from the group consisting of the general formulae (2), (3) and (4)

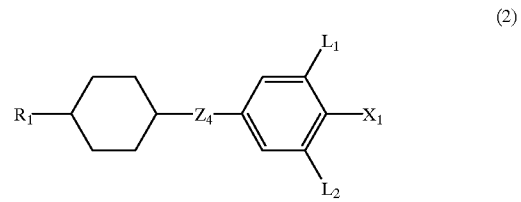

(2)

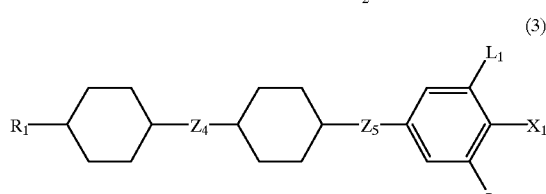

(3)

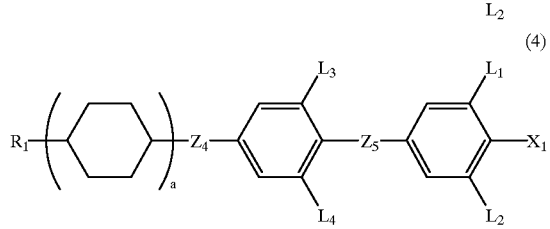

(4)

wherein, $R_1$ denotes an alkyl group having 1 to 10 carbon atoms; $X_1$ denotes F, Cl, $OCF_3$, $OCF_2H$, $CF_3$, $CF_2H$ or $CFH_2$; $L_1$, $L_2$, $L_3$ and $L_4$ denote each independently H or F; $Z_4$ and $Z_5$ denote each independently —$(CH_2)_2$—, —CH=CH— or a covalent bond; and a denotes 1 or 2, is (are) contained as the second component.

(14) A liquid crystal composition characterized in that at least one liquid crystalline compound(s) expressed by the general formula (1)

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —$(CH_2)_2$—, —$(CH)_4$—, —CH=CH, —C≡C—, —COO—, —OCO—, —$CH_2O$—, —$OCH_2$—, —CF=CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, is (are) contained as the first component, and that at least one compound(s) selected from the group consisting of the general formulae (5), (6), (7), (8) and (9)

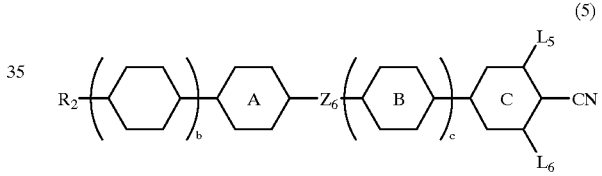

(5)

wherein, $R_2$ denotes F, an alkyl group having 1 to 10 carbon atoms or an alkenyl group having 2 to 10 carbon atoms, in which optional methylene group(s) (—$CH_2$—) in the said alkyl group or alkenyl group may be substituted with (an) oxygen atom(s) (—O—) but two or more than two methylene groups may not be substituted with oxygen atoms consecutively; ring A denotes trans-1,4-cyclohexylene group, 1,4-phenylene group, pyrimidine-2,5-diyl group or 1,3-dioxane-2,5-diyl group; ring B denotes trans-1,4-cyclohexylene group, 1,4-phenylene group or pyrimidine-2,5-diyl group; ring C denotes trans-1,4-cyclohexylene group or 1,4-phenylene group; $Z_6$ denotes —$(CH_2)_2$—, —COO— or a covalent bond; $L_5$ and $L_6$ denote each independently H or F; and b and c denote each independently 0 or 1,

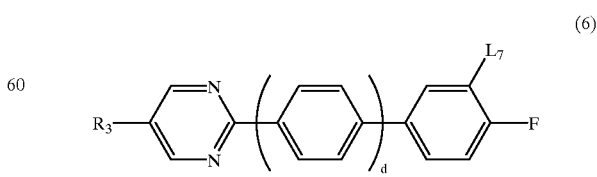

(6)

wherein, $R_3$ denotes an alkyl group having 1 to 10 carbon atoms; $L_7$ denotes H or F; and d denotes 0 or 1, (7)

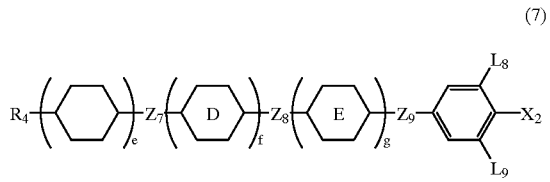

wherein, $R_4$ denotes an alkyl group having 1 to 10 carbon atoms; ring D and ring E denote each independently trans-1,4-cyclohexylene group or 1,4-phenylene group; $Z_7$ and $Z_8$ denote each independently —COO— or a covalent bond; $Z_9$ denotes —COO— or —C≡C—; $L_8$ and $L_9$ denote each independently H or F; $X_2$ denotes F, $OCF_3$, $OCF_2H$, $CF_3$, $CF_2H$ or $CFH_2$; and e, f and g denote each independently 0 or 1, (8)

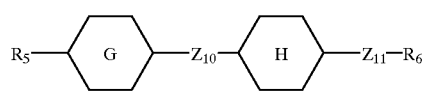

wherein, $R_5$ and $R_6$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring G denotes trans-1,4-cyclohexylene group, 1,4-phenylene group or pyrimidine-2,5-diyl group; ring H denotes trans-1,4-cyclohexylene group or 1,4-phenylene group; $Z_{10}$ denotes —C≡C—, —COO—, —($CH_2$)$_2$—, —CH=CH—C≡C— or a covalent bond; and $Z_{11}$ denotes —COO— or a covalent bond, (9)

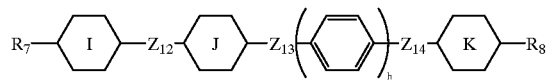

wherein, $R_7$ and $R_8$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring I denotes trans-1,4-cyclohexylene group, 1,4-phenylene group or pyrimidine-2,5-diyl group; ring J denotes trans-1,4-cyclohexylene group, 1,4-phenylene group in which one or more than one hydrogen atom(s) on ring may be substituted with F, or pyrimidine-2,5-diyl group; ring K denotes trans-1,4-cyclohexylene group or 1,4-phenylene group; $Z_{12}$ and $Z_{14}$ denote each independently —COO—, —($CH_2$)$_2$— or a covalent bond; $Z_{13}$ denotes —CH=CH—, —C≡C—, —COO— or a covalent bond; and h denotes 0 or 1, is (are) contained as the second component.

(15) A liquid crystal composition and a liquid crystal display device using the said comosition characterized in that at least one liquid crystalline compound(s) expressed by the general formula (1)

(1)

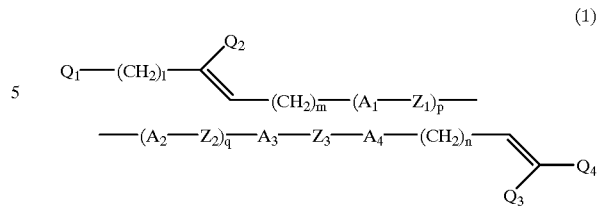

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —($CH_2$)$_2$—, —($CH_2$)$_4$—, —CH=CH—, —C≡C—, —COO—, —OCO—, —$CH_2$O—, —O$CH_2$—, —CF=CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, is (are) contained as the first component, that at least one compound(s) selected from the group consisting of the general formulae (2), (3) and (4)

(2)

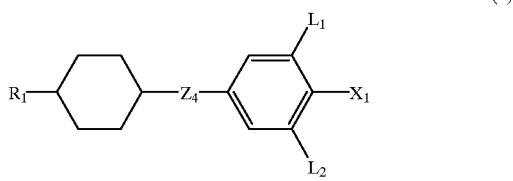

(3)

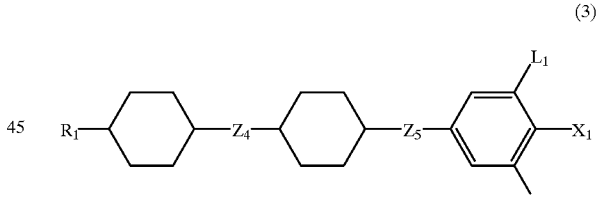

(4)

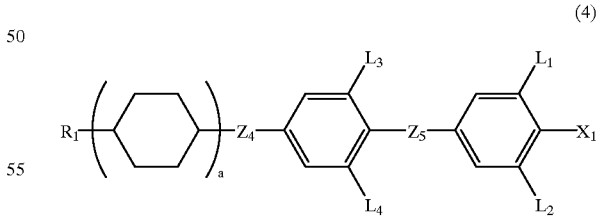

wherein, $R_1$ denotes an alkyl group having 1 to 10 carbon atoms; $X_1$ denotes F, Cl, $OCF_3$, $OCF_2H$, $CF_3$, $CF_2H$ or $CFH_2$; $L_1$, $L_2$, $L_3$ and $L_4$ denote each independently H or F; $Z_4$ and $Z_5$ denote each independently —($CH_2$)$_2$—, —CH=CH— or a covalent bond; and a denotes 1 or 2, is (are) contained as one part of the second component, and that at least one compound(s) selected from the group consisting of the general formulae (5), (6), (7), (8) and (9)

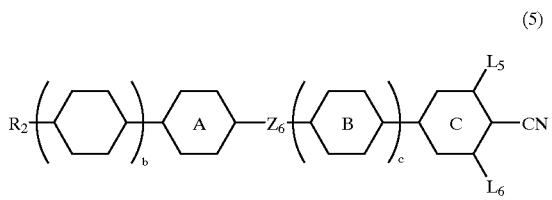

(5)

wherein, $R_2$ denotes F, an alkyl group having 1 to 10 carbon atoms or an alkenyl group having 2 to 10 carbon atoms, in which optional methylene group(s) (—$CH_2$—) in the said alkyl group or alkenyl group may be substituted with (an) oxygen atom(s) (—O—) but two or more than two methylene groups may not be substituted with oxygen atoms consecutively; ring A denotes trans-1,4-cyclohexylene group, 1,4-phenylene group, pyrimidine-2,5-diyl group or 1,3-dioxane-2,5-diyl group; ring B denotes trans-1,4-cyclohexylene group, 1,4-phenylene group or pyrimidine-2,5-diyl group; ring C denotes trans-1,4-cyclohexylene group or 1,4-phenylene group; $Z_6$ denotes —$(CH_2)_2$—, —COO— or a covalent bond; $L_5$ and $L_6$ denote each independently H or F; and b and c denote each independently 0 or 1,

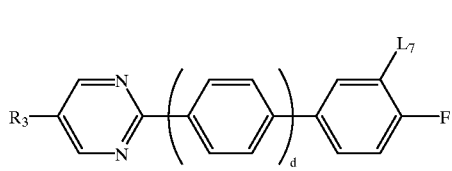

(6)

wherein, $R_3$ denotes an alkyl group having 1 to 10 carbon atoms; $L_7$ denotes H or F; and d denotes 0 or 1,

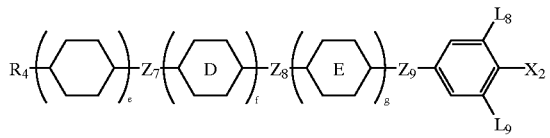

(7)

wherein, $R_4$ denotes an alkyl group having 1 to 10 carbon atoms; ring D and ring E denote each independently trans-1,4-cyclohexylene group or 1,4-phenylene group; $Z_7$ and $Z_8$ denote each independently —COO— or a covalent bond; $Z_9$ denotes —COO— or —C≡C—; $L_8$ and $L_9$ denote each independently H or F; $X_2$ denotes F, $OCF_3$, $OCF_2H$, $CF_3$, $CF_2H$ or $CFH_2$; and e, f and g denote each independently 0 or 1,

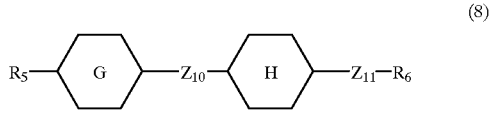

(8)

wherein, $R_5$ and $R_6$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring G denotes trans-1,4-cyclohexylene group, 1,4-phenylene group or pyrimidine-2,5-diyl group; ring H denotes trans-1,4-cyclohexylene group or 1,4-phenylene group; $Z_{10}$ denotes —C≡C—, —COO—, —$(CH_2)_2$—, —CH=CH—C≡C— or a covalent bond; and $Z_{11}$ denotes —COO— or a covalent bond,

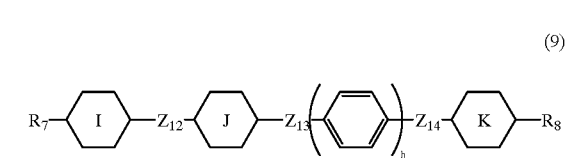

(9)

wherein, $R_7$ and $R_8$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring I denotes trans-1,4-cyclohexylene group, 1,4-phenylene group or pyrimidine-2,5-diyl group; ring J denotes trans-1,4-cyclohexylene group, 1,4-phenylene group in which one or more than one hydrogen atom(s) on ring may be substituted with F, or pyrimidine-2,5-diyl group; ring K denotes trans-1,4-cyclohexylene group or 1,4-phenylene group; $Z_{12}$ and $Z_{14}$ denote each independently —COO—, —$(CH_2)_2$— or a covalent bond; $Z_{13}$ denotes —CH=CH—, —C≡C—, —COO— or a covalent bond; and h denotes 0 or 1, is (are) contained as the second component.

Best Mode for Carrying Out the Invention

Liquid crystalline compounds expressed by the general formula (1) according to the invention are characterized in that they are bicyclic to tetracyclic type derivatives having an alkenyl group substituted by (a) halogen atom(s) and an alkenyl group as substituents on both terminals of molecule. These liquid crystalline compounds are stable physically and chemically under conditions in which display devices being used, and in addition they are characterized to have a wide liquid crystal phase temperature range, a good solubility into liquid crystal compositions even at a lower temperature, a low viscosity and a high elastic constant ratio $K_{33}/K_{11}$. Furthermore, desired physical properties can be optionally adjusted by selecting adequately ring structures, bonding groups or sutructures of side chains among molecular constitutional factors. Thus, in the case that the compounds of the invention being used as components of liquid crystal compositions, they show good characteristics, in more detail, 1) They have wide liquid crystal phase temperature range in spite of containing alkenyl group.
2) There are obtained decrease in a threshold voltage and improvement in a response speed due to a low viscosity.
3) Nematic liquid crystal composition can be prepared without any deposition of crystals and any appearance of a smectic phase at an extremely low temperature.
4) A high contrast can be obtained due to improvement in an elastic constant ratio $K_{33}/K_{11}$.

As well as, they are stable against external enveironments and also they can provide novel liquid crystal compositions and liquid crystal display devices by which enlargement of the used temperature range, a driving property at low voltage, a high speed response and a high contrast can be realized.

Compounds having an alkenyl group substituted by (a) halogen(s) independently as a molecular terminal group are disclosed already in Toku-Kai-Hei 1-175947 and Toku-Kai- Hei 1-308239 etc. These compounds are however have strong appearances of smectic phases and narrow liquid crystal phase temperature ranges. Furthermore, elastic constant ratios $K_{33}/K_{11}$ cannot be mentioned to be high. Although it is needless to say that the compounds of the invention all show preferable physical properties, liquid crystal compositions according to objects can be prepared by using compounds of the formula (1) in which $A_1, A_2, A_3, A_4$, $Z_1, Z_2, Z_3, Q_1, Q_2, Q_3, Q_4$, 1, m, n, p and q are adequately selected.

That is, in the case for use in liquid crystal compositions in which a temperature range to appear liquid crystal phase being higher side of the temparature range, tetracyclic type compounds wherein p=q=1 may be used, and in other cases, bicyclic type or tricyclic type compounds may be used, and in particular, in the case of compounds with a low viscosity being necessary, bicyclic type compounds wherein $A_3$ and $A_4$ are trans-1,4-cyclohexylene groups may be used. Furthermore, those with fluorine substituted on 1,4-phenylene group show particularly superior solubility at a lower temperature.

Furthermore, if an appropriate refractive anisotropy value being necessary, those wherein $A_1$, $A_2$, $A_3$ and $A_4$ are 1,4-phenylene groups, and $Z_1$, $Z_2$ and $Z_3$ are covalent bonds may be selected adequately.

Hereinbelow, $R_9$ is a group shown as follows:

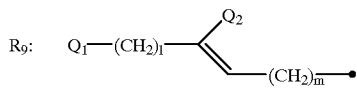

Hereinbelow, $R_{10}$ is a group shown as follows:

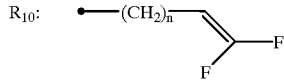

Cyc mentioned later denotes trans-1,4-cyclohexylene group, Phe denotes 1,4-phenylene group in which one or more than one hydrogen atom(s) on six-membered rings may be substituted by (a) halogen atom(s), and compounds of the general formula (1) according to the invention are classified as follows.

Compounds having two six-membered rings $R_9$-$A_3$-$A_4$-$R_{10}$ (1a)

$R_9$-$A_3$-$Z_3$-$A_4$-$R_{10}$ (1b)

Compounds having three six-membered rings $R_9$-$A_2$-$A_3$-$A_4$-$R_{10}$ (1c)

$R_9$-$A_2$-$Z_2$-$A_3$-$A_4$-$R_{10}$ (1d)

$R_9$-$A_2$-$A_3$-$Z_3$-$A_4$-$R_{10}$ (1e)

$R_9$-$A_2$-$Z_2$-$A_3$-$Z_3$-$A_4$-$R_{10}$ (1f)

Compounds having four six-membered rings $R_9$-$A_1$-$A_2$-$A_3$-$A_4$-R10 (1g)

$R_9$-$A_1$-$Z_1$-$A_2$-$A_3$-$A_4$-$R_{10}$ (1h)

$R_9$-$A_1$-$A_2$-$Z_2$-$A_3$-$A_4$-$R_{10}$ (1i)

$R_9$-$A_1$-$A_2$-$A_3$-$Z_3$-$A_4$-$R_{10}$ (1j)

$R_9$-$A_1$-$Z_1$-$A_2$-$Z_2$-$A_3$-$A_4$-$R_{10}$ (1k)

$R_9$-$A_1$-$Z_1$-$A_2$-$A_3$-$Z_3$-$A_4$-$R_{10}$ (1l)

$R_9$-$A_1$-$A_2$-$Z_2$-$A_3$-$Z_3$-$A_4$-$R_{10}$ (1m)

$R_9$-$A_1$-$Z_1$-$A_2$-$Z_2$-$A_3$-$Z_3$-$A_4$-$R_{10}$ (1n)

Among these compounds, compounds expressed by the formulae (1a), (1c) and (1g) are particularly prefarable for attaining objects of the invention.

Compounds expressed by the formula (1a) are classified still more into compounds expressed by the following formulae (1aa) to (1ac).

$R_9$-Cyc-Cyc-$R_{10}$ (1aa)

$R_9$-Phe-Cyc-$R_{10}$ (1ab)

$R_9$-Phe-Phe-$R_{10}$ (1ac)

Among these compounds, compounds expressed by the formulae (1aa) and (1ab) are particularly prefarable. These bicyclic type comopunds show wide liquid crystal phase temperature ranges, eminently low viscosities and high elastic constant ratios $K_{33}/K_{11}$, as well as they can lower only viscosities eminently without lowering clearing points in the case for use in liquid crystal compositions.

Furthermore, compounds expressed by the formula (1c) are classified still more into compounds expressed by the following formulae (1ca) to (1cd).

$R_9$-Cyc-Cyc-Cyc-$R_{10}$ (1ca)

$R_9$-Phe-Cyc-Cyc-$R_{10}$ (1cb)

$R_9$-Phe-Phe-Cyc-$R_{10}$ (1cc)

$R_9$-Phe-Phe-Phe-$R_{10}$ (1cd)

Among these compounds, compounds expressed by the formulae (1ca), (1cb) and (1cc) are particularly prefarable. Althogh these tricyclic type compounds also show similar properties as bicyclic type compounds, they can set higher clearing points in the case of use in liquid crystal compositions.

Furthermore, compounds expressed by the formula (1g) are classified still more into compounds expressed by the following formulae (1ga) to (1gc).

$R_9$-Cyc-Cyc-Cyc-Cyc-$R_{10}$ (1ga)

$R_9$-Cyc-Phe-Phe-Cyc-$R_{10}$ (1gb)

$R_9$-Cyc-Phe-Phe-Phe-$R_{10}$ (1gc)

Among these compounds, compounds expressed by the formula (1gb) are particularly prefarable. These tetracyclic type compounds have not only high clearing points but also relatively low viscosities, and also they can increase only clearing point with maintaining viscosities in the case for use in liquid crystal compositions.

As described above, compounds expressed by the formulae (1aa), (1ab), (1ca), (1cb), (1cc) and (1gb) are particularly preferable examples, and among them, compounds expressed by the following formulae (1-1) to (1-5) are mentioned as more preferable ones.

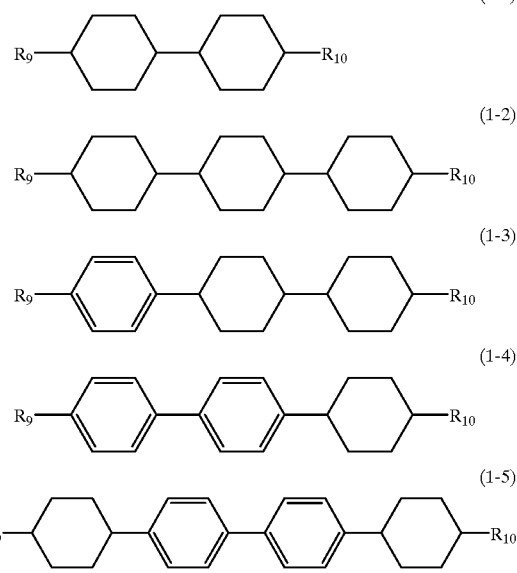

In all compounds described above, $R_9$ is an alkenyl group having 2 to 12 carbon atoms in which (an) optional H atom(s) may be substituted by F atom(s), and among them, the followings are particularly preferable: vinyl, 1-propenyl, 2-propenyl, 1-butenyl, 2-butenyl, 3-butenyl, 1-pentenyl, 2-pentenyl, 3-pentenyl, 4-pentenyl, 1,5-hexadienyl, 2-fluoroethenyl, 3-fluoro-1-propenyl, 3-fluoro-2-propenyl, 4-fluoro-1-butenyl, 4-fluoro-2-butenyl, 4-fluoro-3-butenyl, 5-fluoro-1-pentenyl, 5-fluoro-2-pentenyl, 5-fluoro-3-pentenyl, 5-fluoro-4-pentenyl, 2,2-difluoroethenyl, 3,3-difluoro-2-propenyl, 4,4-difluoro-3-butenyl, 5,5-difluoro-4-pentenyl and 6,6-difluoro-5-hexenyl.

Furthermore, $R_{10}$ is a difluoroalkenyl group having 2 to 7 carbon atoms in which (an) optional F atom(s) may be substituted by Cl atom(s), and among them, the followings are particularly preferable: 2,2-difluoroethenyl, 3,3-difluoro-2-propenyl, 4,4-difluoro-3-butenyl, 5,5-difluoro-4-pentenyl, 6,6-difluoro-5-hexenyl, 7,7-difluoro-6-heptenyl, 2-chloro-2-fluoroethenyl, 3-chloro-3-fluoro-2-propenyl, 4-chloro-4-fluoro-3-butenyl, 5-chloro-5-fluoro-4-pentenyl, 6-chloro-6-fluoro-5-hexenyl and 7-chloro-7-fluoro-6-heptenyl.

Liquid crystal compositions according to the invention preferably contain one or more than one compound(s) expressed by (1) in a proportion of 0.1 to 99.9% by weight, in order to show superior properties.

In more detail, liquid crystal compositions provided by the invention are accomplished by mixing the first component which contains at least one compound(s) (1) with (an) optional compound(s) selected from other compound groups or those of the general formulae (2) to (9), according to objects of the liquid crystal compositions.

Although liquid crystal compositions provided by the invention may be consisted of the first component which contains at least one liquid crystalline compound(s) shown by the general formula (1), those obtained by mixing the component with at least one component(s) (hereinafter referred to the second A component) selected from the above-mentioned general formulae (2), (3) and (4) and/or at least one component(s) (hereinafter referred to the second B component) selected from the above-mentioned general formulae (5), (6), (7), (8) and (9) as the second components, and also (a) known compound(s) may be mixed in as the third component with the intention of adjusting a threshold voltage, a liquid crystal phase temperature range, a refractive anisotropy value, a dielectric anisotropy value and a viscosity etc.

Among the above-mentioned second A components, there may be mentioned (2-1) to (2-15), (3-1) to (3-48) and (4-1) to (4-55) as preferable examples of compounds of the general formulae (2), (3) and (4), respectively.

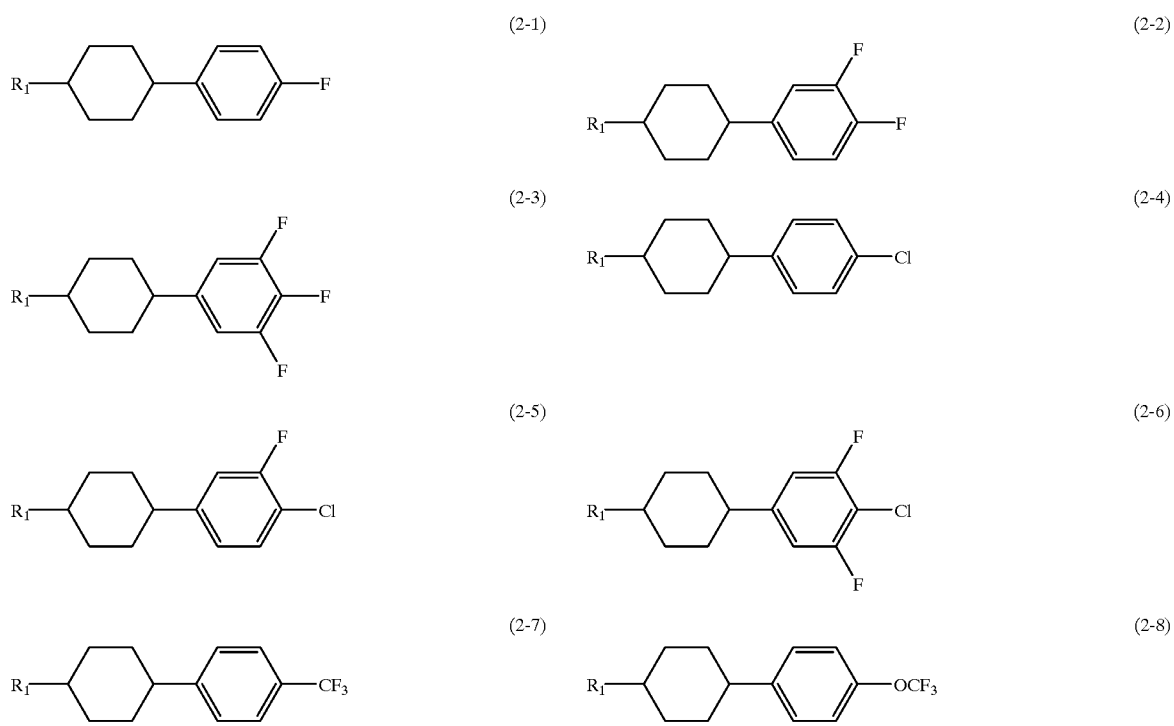

(2-9) 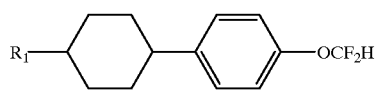
(2-10) 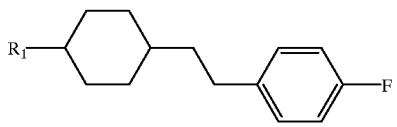
(2-11) 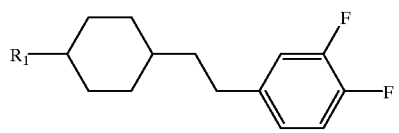
(2-12) 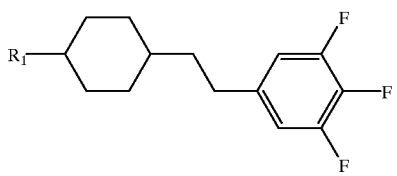
(2-13) 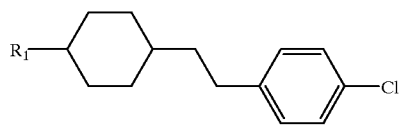
(2-14) 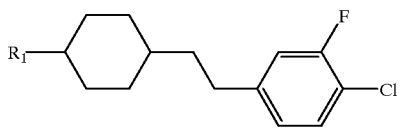
(2-15) 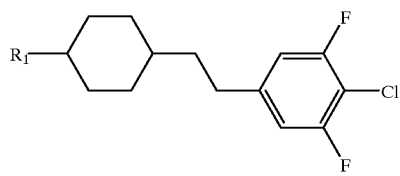
(3-1) 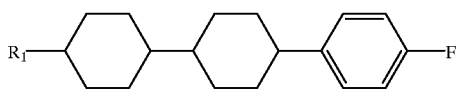
(3-2) 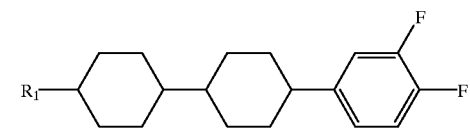
(3-3) 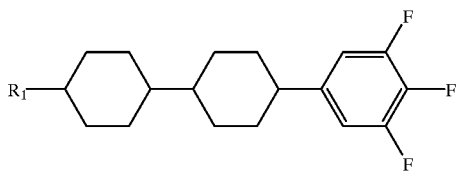
(3-4) 
(3-5) 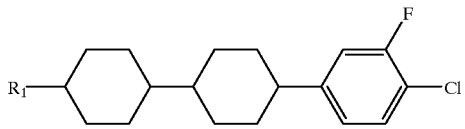
(3-6) 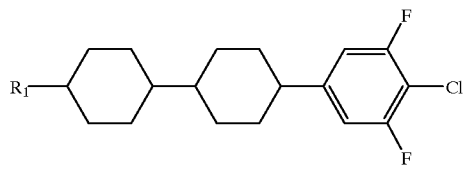
(3-7) 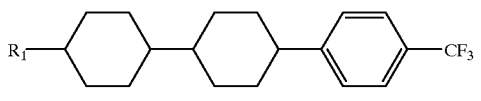
(3-8) 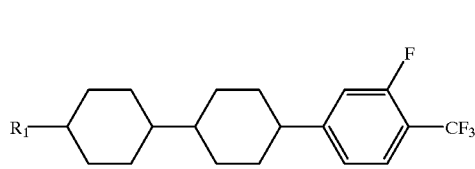
(3-9) 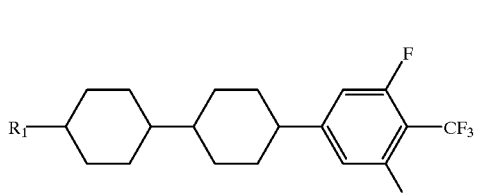
(3-10) 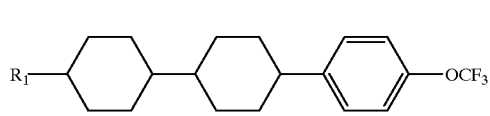
(3-11) 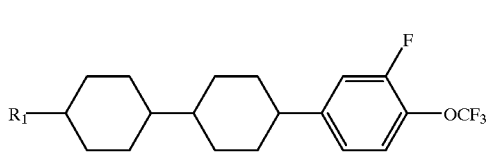

-continued
(3-12) 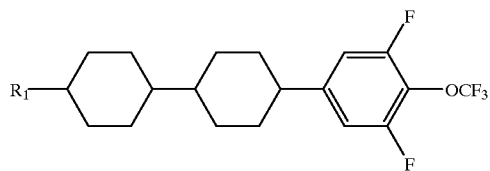
(3-13) 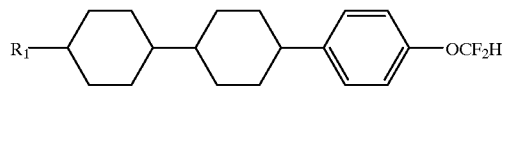
(3-14) 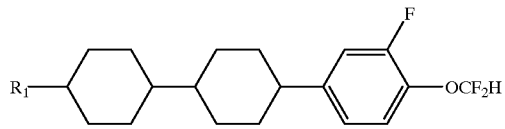
(3-15) 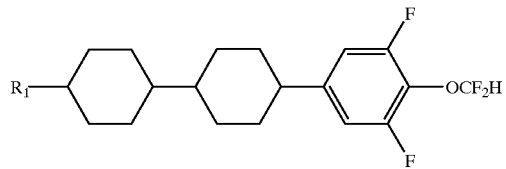
(3-16) 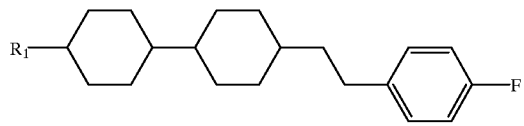
(3-17) 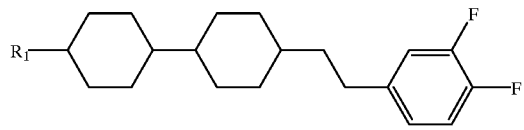
(3-18) 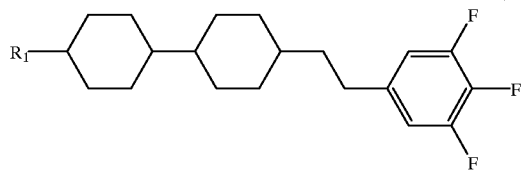
(3-19) 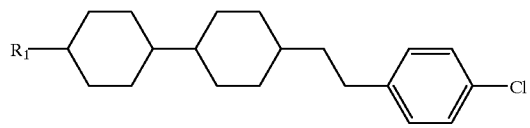
(3-20) 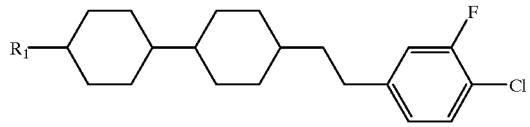
(3-21) 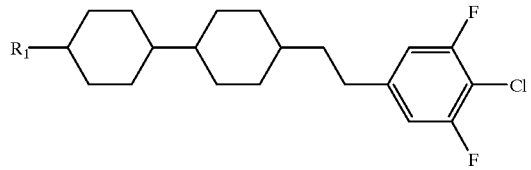
(3-22) 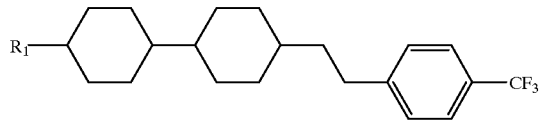
(3-23) 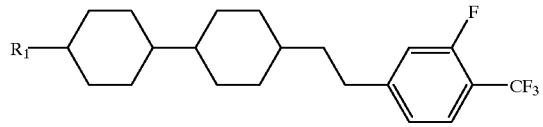
(3-24) 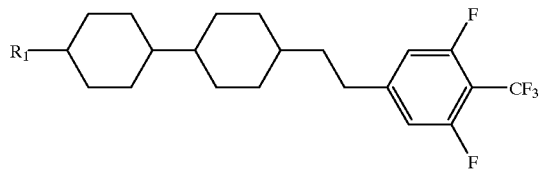
(3-25) 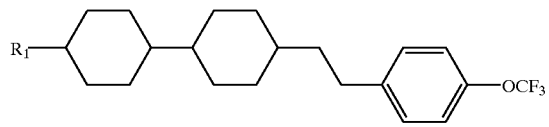
(3-26) 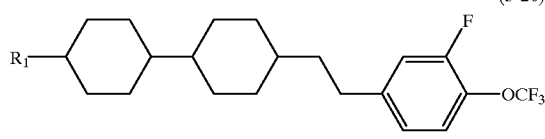
(3-27) 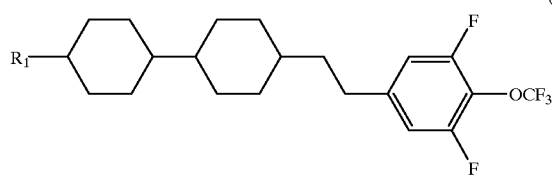

-continued
(3-28)
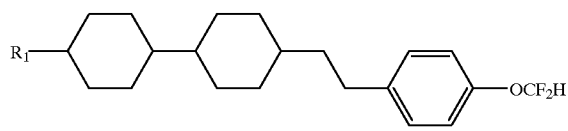
(3-29)
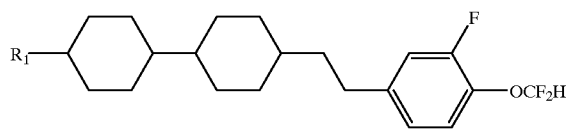
(3-30)
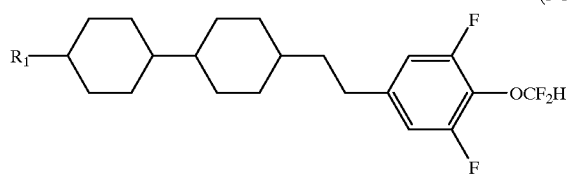
(3-31)
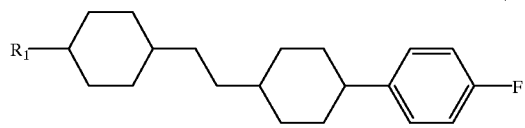
(3-32)
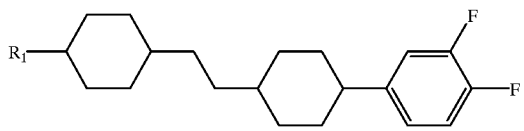
(3-33)
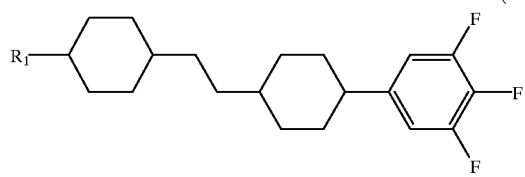
(3-34)
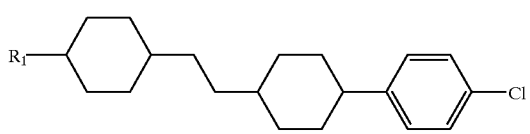
(3-35)
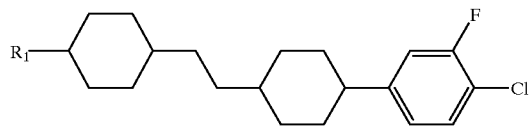
(3-36)
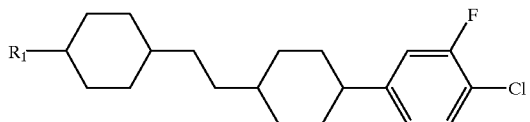
(3-37)
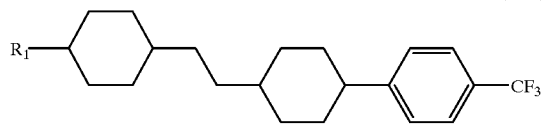
(3-38)
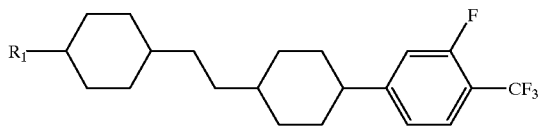
(3-39)
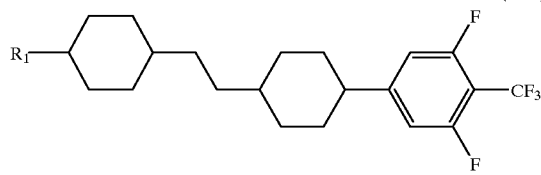
(3-40)
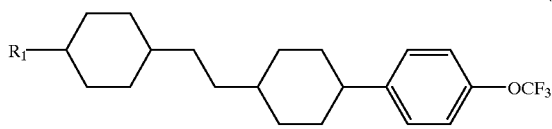
(3-41)
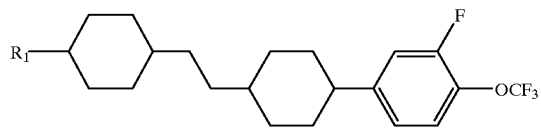
(3-42)
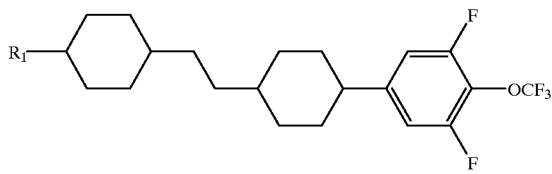

(3-43)
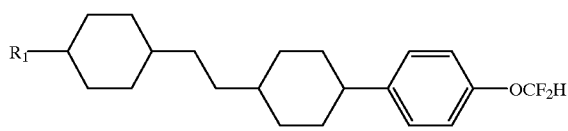
(3-44)
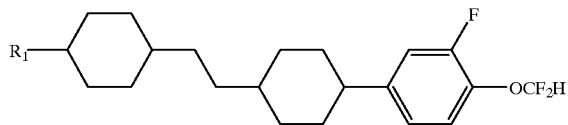
(3-45)
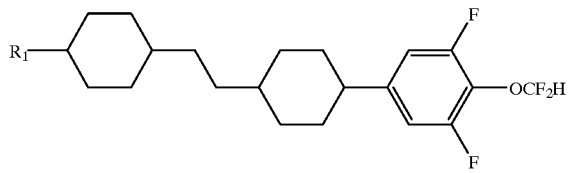
(3-46)
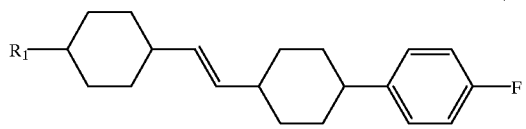
(3-47)
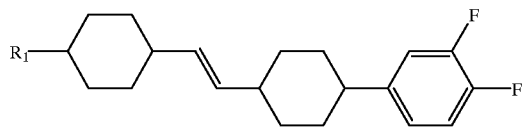
(3-48)
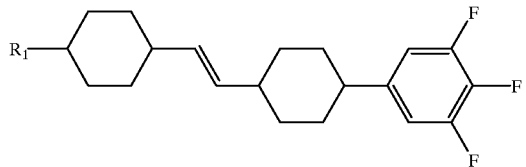
(4-1)
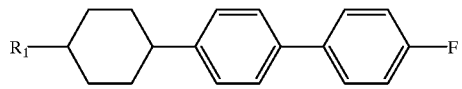
(4-2)
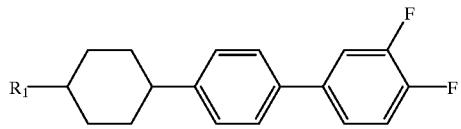
(4-3)
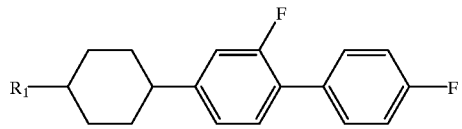
(4-4)
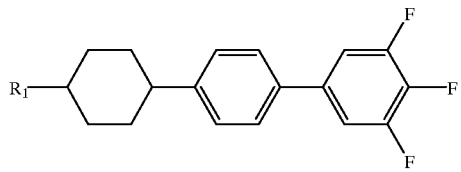
(4-5)
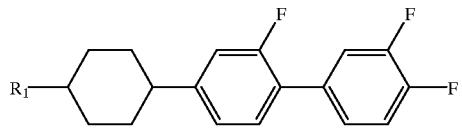
(4-6)
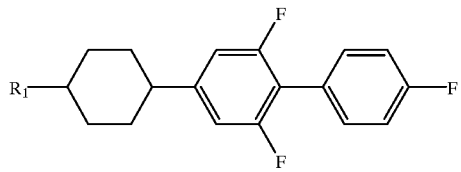
(4-7)
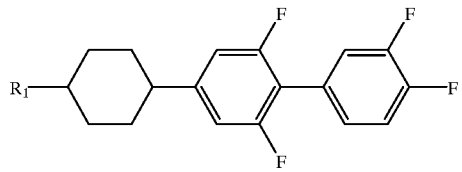
(4-8)
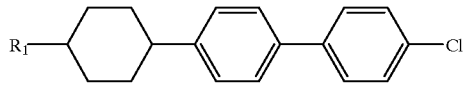
(4-9)
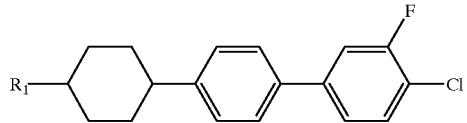

-continued
(4-10) 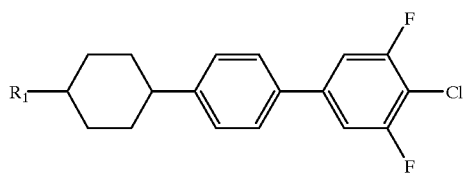
(4-11) 
(4-12) 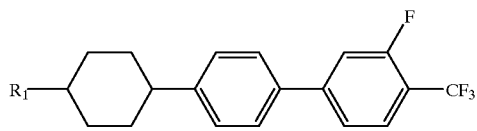
(4-13) 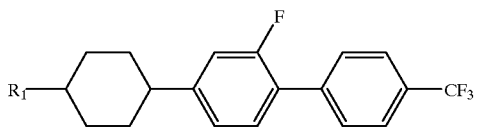
(4-14) 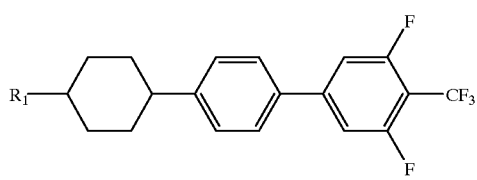
(4-15) 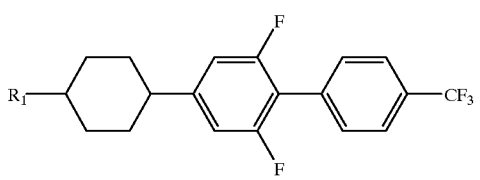
(4-16) 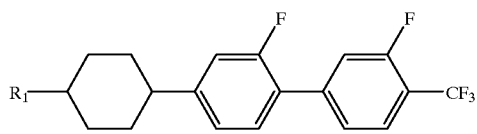
(4-17) 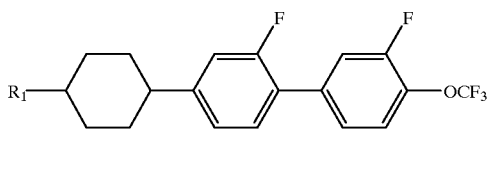
(4-18) 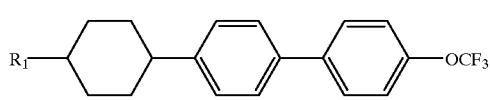
(4-19) 
(4-20) 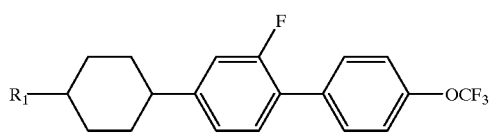
(4-21) 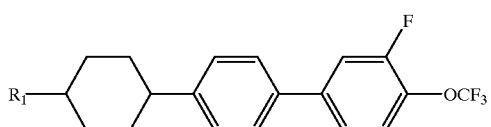
(4-22) 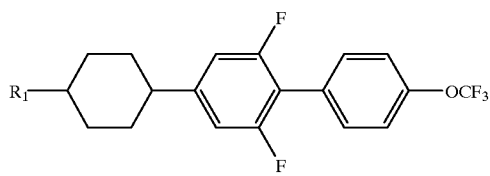
(4-23) 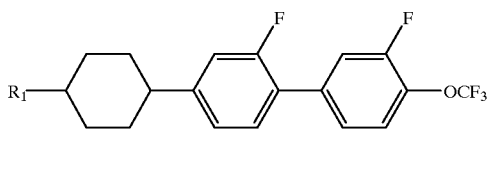
(4-24) 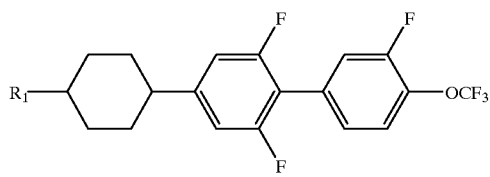
(4-25) 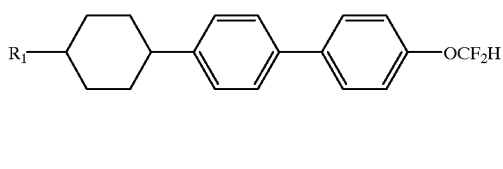
(4-26) 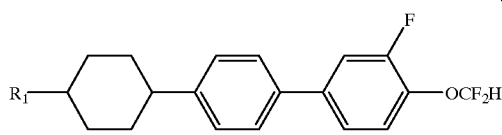
(4-27)

-continued

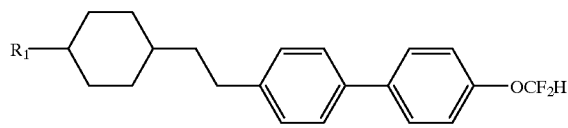
(4-46)
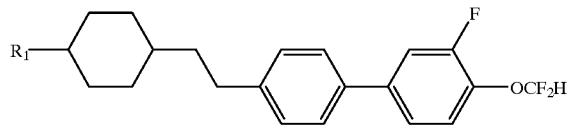
(4-47)
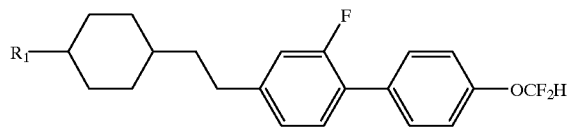
(4-48)
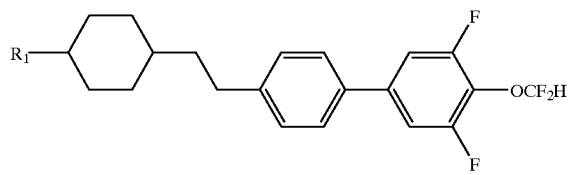
(4-49)
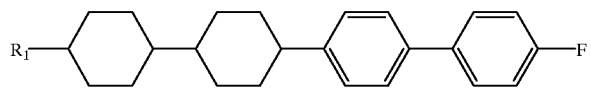
(4-50)
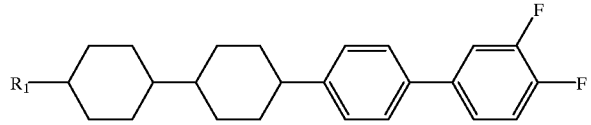
(4-51)
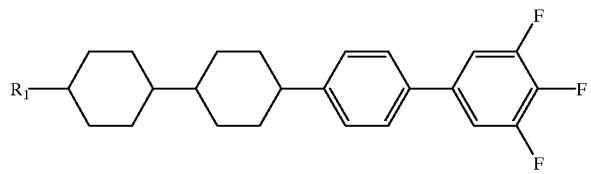
(4-52)
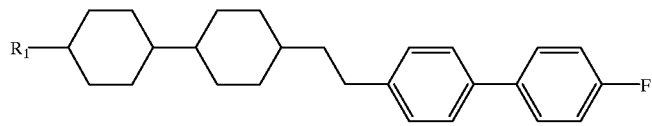
(4-53)
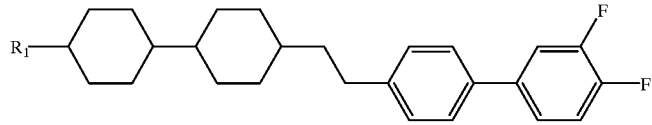
(4-54)
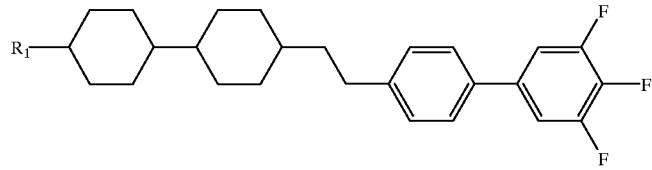
(4-55)

wherein, $R_1$ denotes the same meaning as the above-mentioned one.

Compounds expressed by these general formulae (2) to (4) show positive dielectric anisotropies and they are very superior in heat stability and chemical stability.

An amount of the said compound used is adequately within a range of 1 to 99% by weight, preferably 10 to 97% by weight, and more preferably 40 to 95% by weight, based on the total weight of a liquid crystal composition.

Next, among the above-mentioned second B components, there may be mentioned (5-1) to (5-24), (6-1) to (6-3) and (7-1) to (7-28) as preferable examples of compounds of the general formulae (5), (6) and (7), respectively.

(5-1)
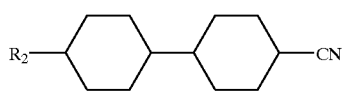

(5-2)
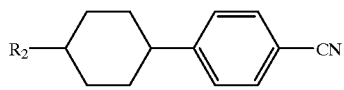

(5-3)
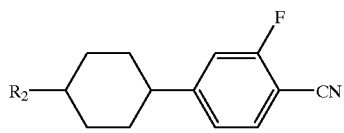

(5-4)
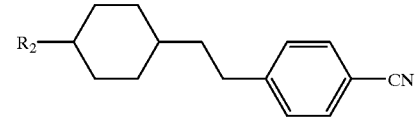

(5-5)
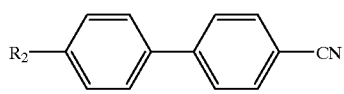

(5-6)
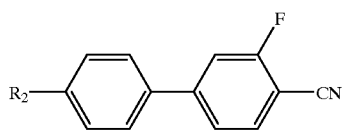

(5-7)
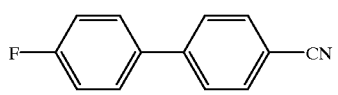

(5-8)
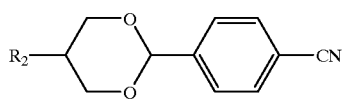

(5-9)
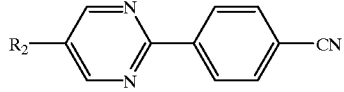

-continued (5-10)
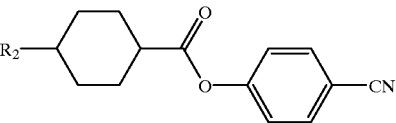

(5-11)
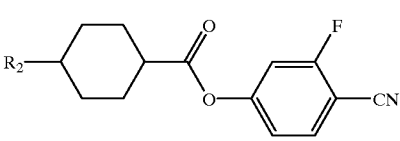

(5-12)
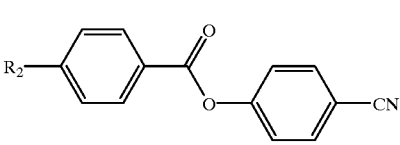

(5-13)
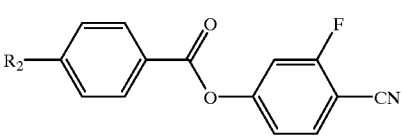

(5-14)
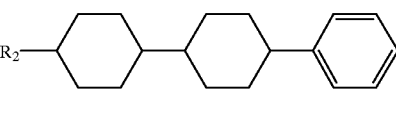

(5-15)
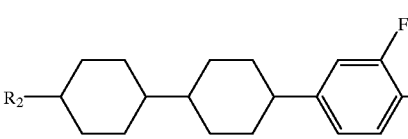

(5-16)
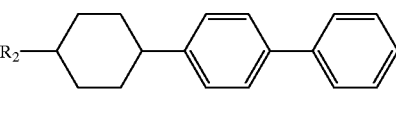

(5-17)
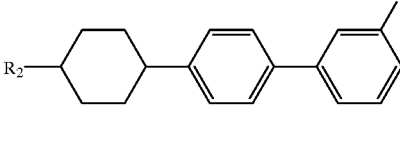

(5-18)
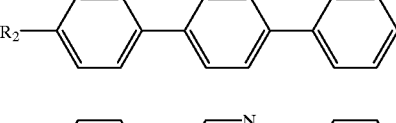

(5-19)
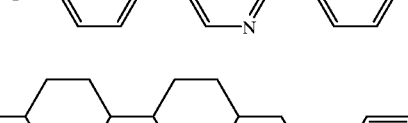

(5-20)

-continued
(5-21)
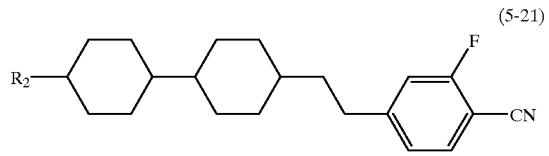
(5-22)
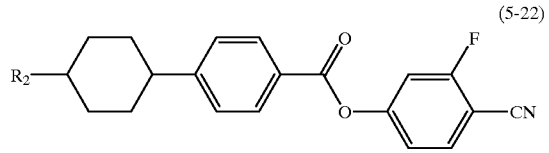
(5-23)
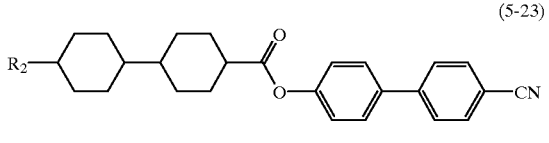
(5-24)
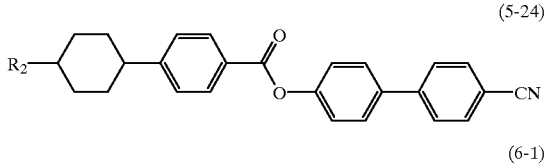
(6-1)
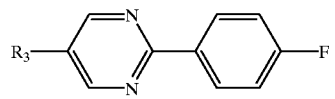
(6-2)
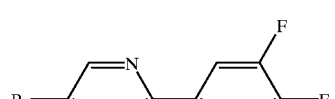
(6-3)
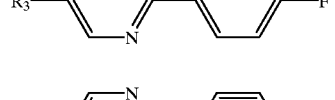
(7-1)
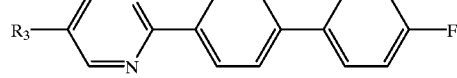
(7-2)
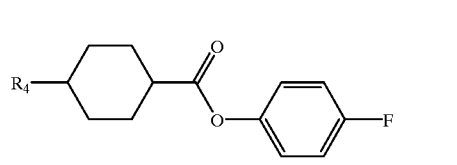
(7-3)
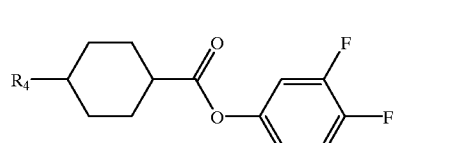
(7-4)
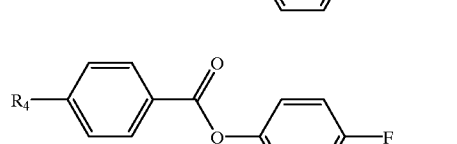
-continued
(7-5)
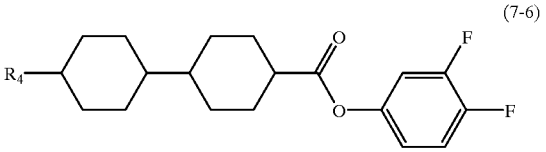
(7-6)
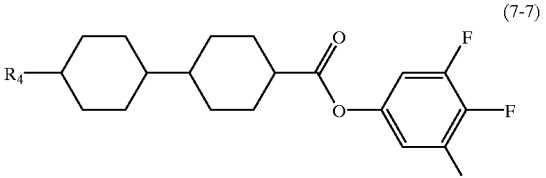
(7-7)
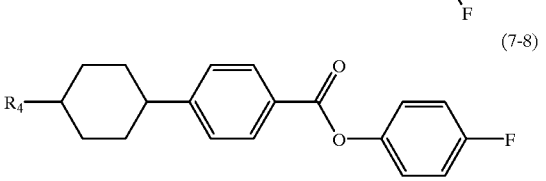
(7-8)
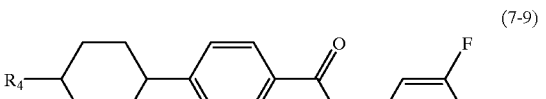
(7-9)
(7-10)
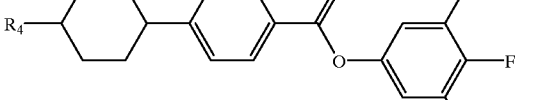
(7-11)
(7-12)
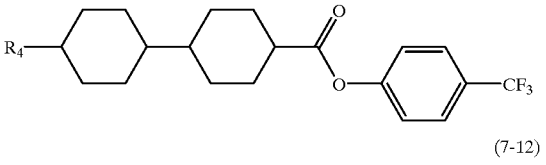
(7-13)
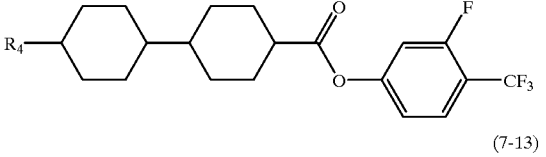
(7-14)
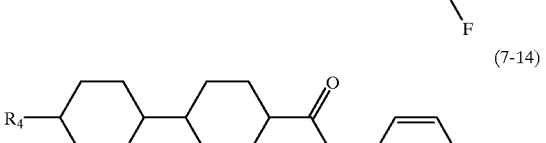

(7-15) 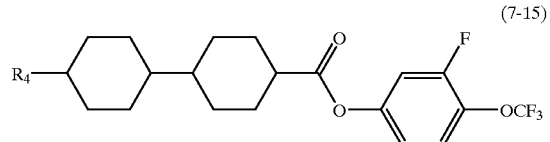

(7-16) 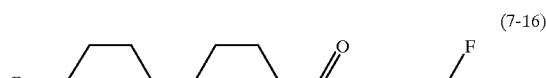

(7-17) 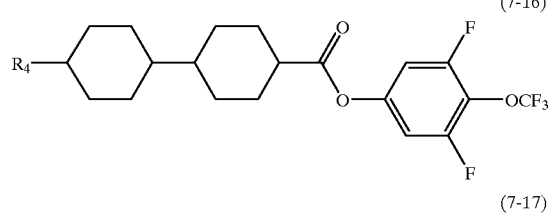

(7-18) 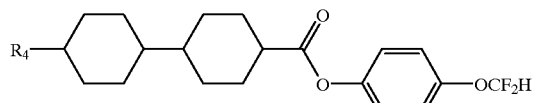

(7-19) 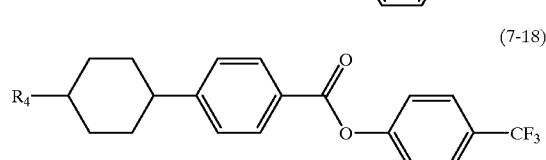

(7-20) 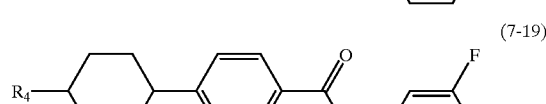

(7-21) 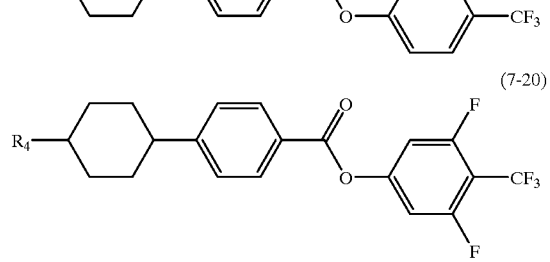

(7-22) 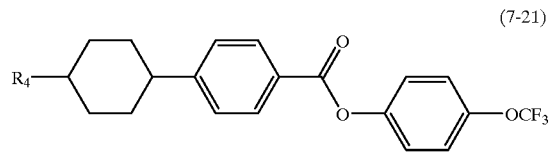

(7-23) 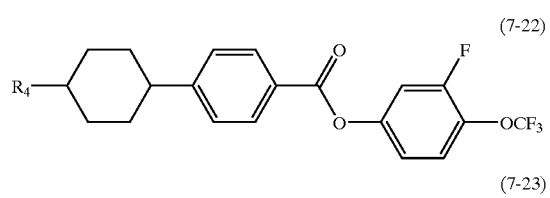

(7-24) 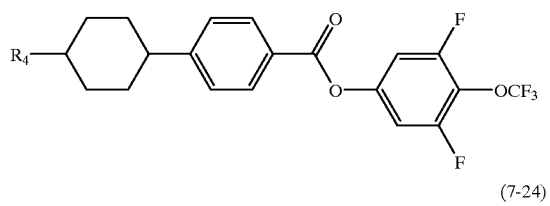

(7-25) 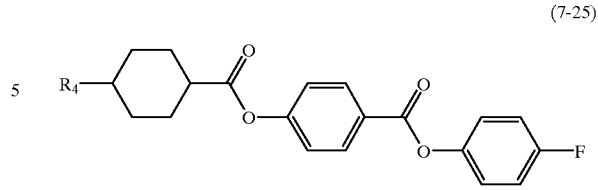

(7-26) 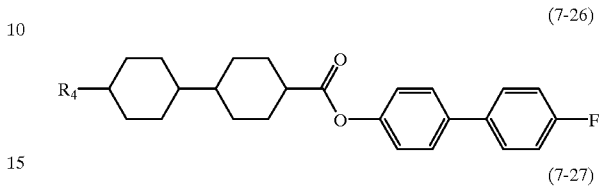

(7-27) 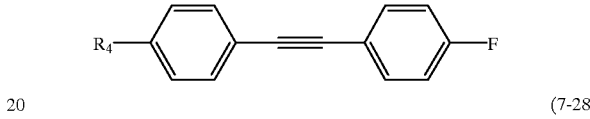

(7-28) 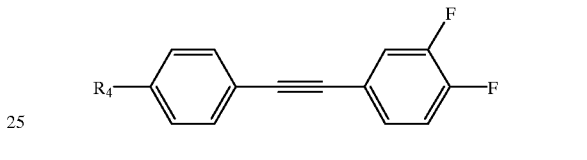

wherein, $R_2$, $R_3$ and $R_4$ denote the same meanings as the above-mentioned ones.

Compounds expressed by these general formulae (5) to (7) show positive dielectric anisotropies and they are particularly used with the intention of lowering a threshold voltage as components of compositions. Furthermore, they are used with the intentions of adjusting a viscosity, adjusting a refractive anisotropy value and enlarging a liquid crystal phase temperature range, as well as with the intention of improvement in sharpness.

Also, among the above-mentioned second B components, there may be mentioned (8-1) to (8-8) and (9-1) to (9-13) as preferable examples of compounds of the general formulae (8) and (9), respectively.

(8-1) 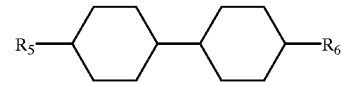

(8-2) 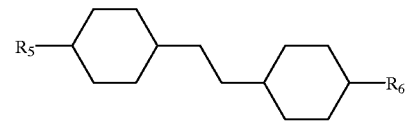

(8-3) 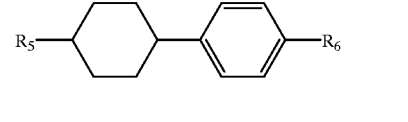

(8-4) 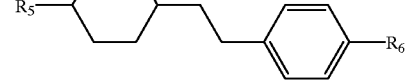

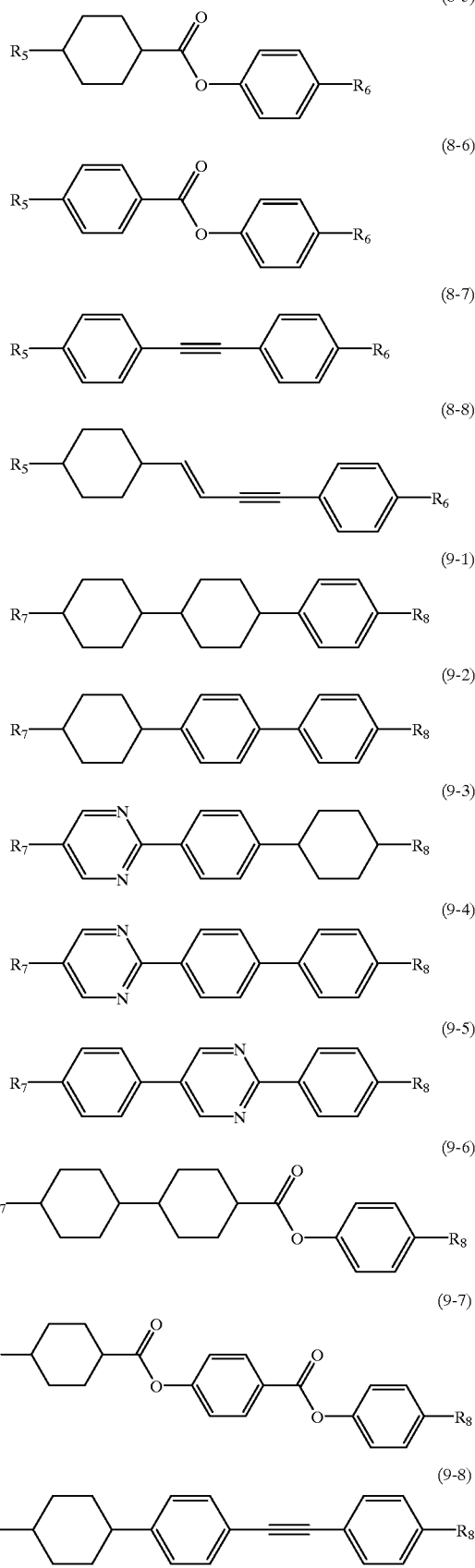
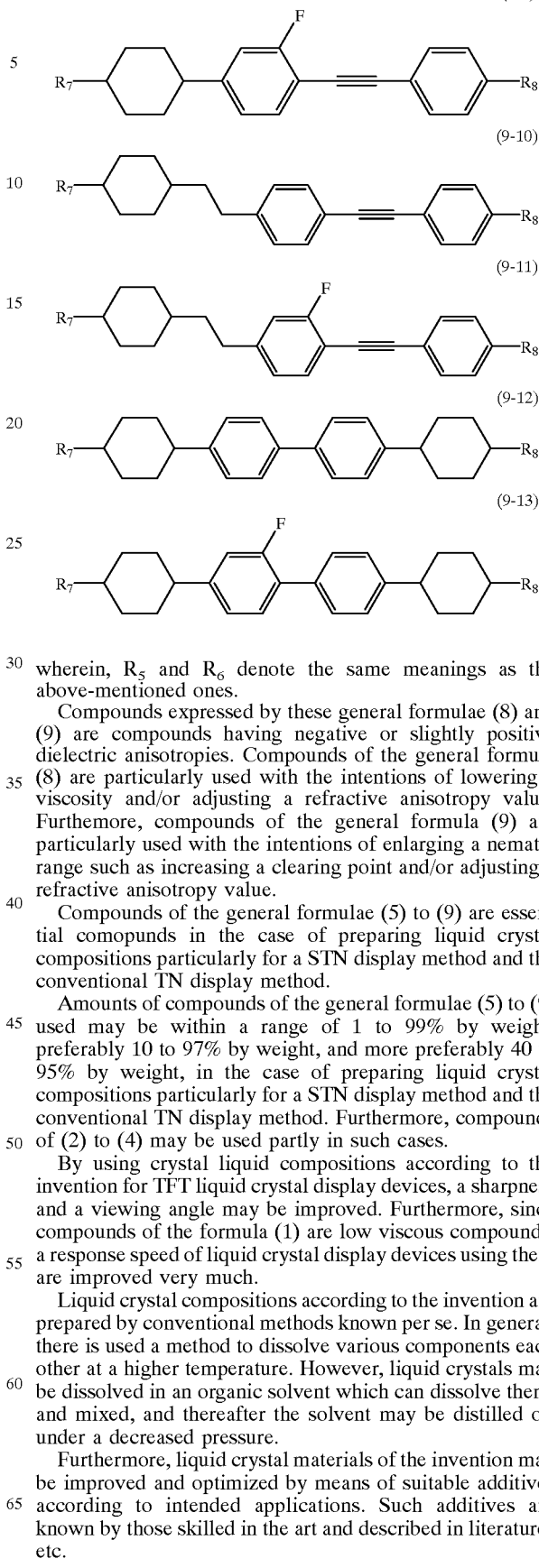

wherein, $R_5$ and $R_6$ denote the same meanings as the above-mentioned ones.

Compounds expressed by these general formulae (8) and (9) are compounds having negative or slightly positive dielectric anisotropies. Compounds of the general formula (8) are particularly used with the intentions of lowering a viscosity and/or adjusting a refractive anisotropy value. Furthemore, compounds of the general formula (9) are particularly used with the intentions of enlarging a nematic range such as increasing a clearing point and/or adjusting a refractive anisotropy value.

Compounds of the general formulae (5) to (9) are essential comopunds in the case of preparing liquid crystal compositions particularly for a STN display method and the conventional TN display method.

Amounts of compounds of the general formulae (5) to (9) used may be within a range of 1 to 99% by weight, preferably 10 to 97% by weight, and more preferably 40 to 95% by weight, in the case of preparing liquid crystal compositions particularly for a STN display method and the conventional TN display method. Furthermore, compounds of (2) to (4) may be used partly in such cases.

By using crystal liquid compositions according to the invention for TFT liquid crystal display devices, a sharpness and a viewing angle may be improved. Furthermore, since compounds of the formula (1) are low viscous compounds, a response speed of liquid crystal display devices using them are improved very much.

Liquid crystal compositions according to the invention are prepared by conventional methods known per se. In general, there is used a method to dissolve various components each other at a higher temperature. However, liquid crystals may be dissolved in an organic solvent which can dissolve them, and mixed, and thereafter the solvent may be distilled off under a decreased pressure.

Furthermore, liquid crystal materials of the invention may be improved and optimized by means of suitable additives according to intended applications. Such additives are known by those skilled in the art and described in literatures etc.

For example, dichromatic dyestuffs such as merocyanine type, styryl type, azoxy type, quinophthalone type, anthraquinone type and tetrazine type etc. may be added to use as liquid crystal compositions for a guest-host (GH) mode. Alternatively, they may be used as liquid crystal compositions for polymer disperse type liquid crystal display decices (PDLCD) represented by NCAP which is prepared by microcapsulating nematic liquid cystals and polymer network liquid crystal display devices (PNLCD) in which three-dimensional network macromolecules being made in liquid crystals. Furthermore, they may be used as liquid crystal compositions for an effective controlled birefringent (ECB) mode and a dinamic scattering (DS) mode.

Furthermore, there may be mentioned the following composition examples (Use Examples 1 to 36) as nematic liquid crystal compositions containing compounds of the invention.

Compounds in composition examples are denoted by abbreviations according to definitions shown in Table 1. Furthermore, constitutions of optically active compounds are as follows.

CM-33

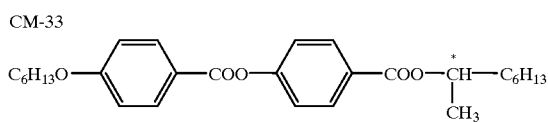

CN

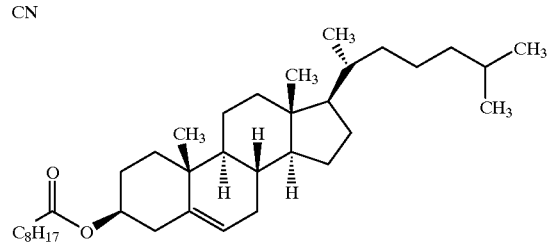

-continued

In composition examples (use examples), "%" denotes "% by weight", and "part" denotes "part by weight" based on 100 parts by weight of a liquid crystal composition, unless otherwise described.

The determination temperature of viscosity ($\eta$) is 20.0° C., the detemination temperature and detemination wave length of refractive anisotropy ($\Delta n$) are 25.0° C. and 589 nm respectively, the determination temperature of threshold voltage (Vth) is 25.0° C., and the determination temperature of pitch is 25.0° C.

TABLE 1

Expression modes of compounds using symbole

| 1) Left terminal R— | Symbol | 3) Bonding group —$Z_1$—, —$Z_n$— | Symbol |
|---|---|---|---|
| $C_nH_{2n+1}$— | n- | —$C_2H_4$— | 2 |
| $C_nH_{2n+1}O$— | nO- | —COO— | E |
| $C_nH_{2n+1}OC_mH_{2m}$— | nOm- | —C≡C— | T |
| $CH_2$=CH— | V- | | |
| $CH_2$=CH$C_nH_{2n}$— | Vn- | | |
| $C_nH_{2n+1}$CH=CH— | nV- | | |
| $C_nH_{2n+1}$CH=CH$C_mH_{2m}$— | nVm- | | |
| $CF_2$=CH— | FFV- | | |
| $CF_2$CH$C_nH_{2n}$— | FFVn- | | |

| 2) Ring structuer —(A$_1$)—, —(A$_n$)— | Symbol | 4) Right terminal —X | Symbol |
|---|---|---|---|
| 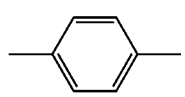 | B | —F | —F |
| | | —Cl | —CL |
| | | —CN | —C |
| | | —OCF$_3$ | —OCF3 |
| 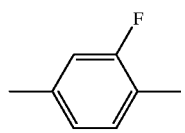 | B (F) | —OCF$_2$H | —OCF2H |
| | | —$C_nH_{2n+1}$ | -n |
| | | —O$C_nH_{2n+1}$ | -On |

TABLE 1-continued

Expression modes of compounds using symbole

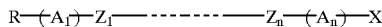

| | | | |
|---|---|---|---|
| 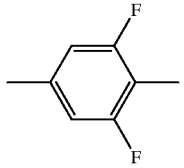 | B (F, F) | —$C_mH_{2m}OC_nH_{2n+1}$ | -mOn |
| 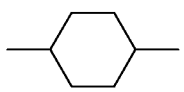 | H | —$COOCH_3$<br>—$CH=CH_2$ | —EMe<br>-V |
| 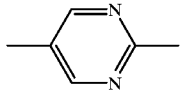 | Py | —$C_nH_{2n}CH=CH_2$<br>—$CH=CHC_nH_{2n+1}$ | -nV<br>-Vn |
| 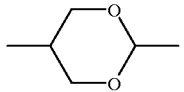 | D | —$C_mH_{2m}CH=CHC_nH_{2n+1}$<br>—$CH=CF_2$<br>—$C_nH_{2n}CH=CF_2$ | -mVn<br>-VFF<br>-nVEF |

5) Expression Examples

Example 1
3-H2B (F, F) B (F) - F

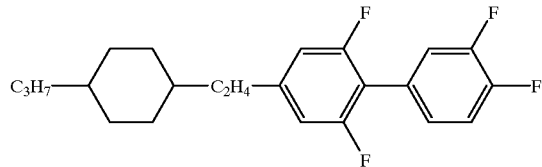

Example 2
1V2 - BEB (F, F) - C

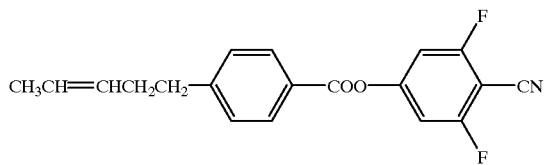

The following examples may be mentioned as nematic liquid crystal compositions containing compounds of the invention.

Use Example 1

| | |
|---|---|
| V2-HH-VFF (No. 25) | 30.0% |
| V-BHH-VFF (No. 7) | 19.0% |
| V-BBH-VFF (No. 9) | 15.0% |
| 3-HB-C | 5.0% |
| 1V2-BEB(F,F)-C | 11.0% |
| 3-HB-O2 | 4.0% |
| 3-HB(F)TB-2 | 4.0% |
| 3-H2BTB-2 | 4.0% |
| 3-H2BTB-3 | 4.0% |
| 3-H2BTB-4 | 4.0% |

-continued

| Use Example 2 | |
|---|---|
| V2-HH-VFF (No. 25) | 20.0% |
| 1V-BHH-VFF (No. 19) | 10.0% |
| V-BBH-VFF (No. 9) | 6.0% |
| 3-HB-C | 10.0% |
| 1V2-BEB(F,F)-C | 12.0% |
| 3-HB-02 | 5.0% |
| 3-HHB-1 | 10.0% |
| 3-HHB-3 | 10.0% |
| 3-HB(F)TB-2 | 5.0% |
| 3-H2BTB-2 | 4.0% |
| 3-H2BTB-3 | 4.0% |
| 3-H2BTB-4 | 4.0% |
| Use Example 3 | |
| 1V-BHH-VFF (No. 19) | 4.0% |
| 1V2-BHH-VFF (No. 118) | 10.0% |
| V2-HB-C | 10.0% |
| 1V2-HB-C | 10.0% |
| 3-HB-C | 26.0% |
| 5-HB-C | 12.0% |
| 3-HB(F)-C | 8.0% |
| 2-BEB-C | 3.0% |
| V2-HHB-1 | 8.0% |
| 3-H2BTB-2 | 3.0% |
| 3-H2BTB-3 | 3.0% |
| 3-H2BTB-4 | 3.0% |
| Use Example 4 | |
| V2-HH-VFF (No. 25) | 9.0% |
| 1V2-BEB(F,F)-C | 11.0% |
| 201-BEB(F)-C | 5.0% |
| 301-BEB(F)-C | 9.0% |
| 3-HB(F)-C | 15.0% |
| 101-HH-3 | 3.0% |
| 4-BTB-02 | 9.0% |
| 2-HHB(F)-C | 13.0% |
| 3-HHB(F)-C | 14.0% |
| 3-H2BTB-2 | 4.0% |
| 3-H2BTB-3 | 4.0% |
| 3-H2BTB-4 | 4.0% |
| Use Example 5 | |
| 1V2-BHH-VFF (No. 118) | 5.0% |
| V-BHH-2VFF (No. 8) | 10.0% |
| V2-HHH-VFF (No. 29) | 5.0% |
| 2-BB-C | 5.0% |
| 2020-BB-C | 4.0% |
| 101-HB-C | 10.0% |
| 201-HB-C | 7.0% |
| 2-BEB-C | 12.0% |
| 5-PyB-F | 8.0% |
| 2-PyB-2 | 2.0% |
| 3-PyB-2 | 2.0% |
| 4-PyB-2 | 2.0% |
| V-HHB-1 | 5.0% |
| 2-PyBH-3 | 5.0% |
| 3-PyBH-3 | 5.0% |
| 4-PyBH-3 | 5.0% |
| 3-PyBB-F | 3.0% |
| 4-PyBB-F | 3.0% |
| 6-PyBB-2 | 2.0% |
| Use Example 6 | |
| V2-HH-VFF (No. 25) | 3.0% |
| 3-PyB(F)-F | 6.0% |
| 3020-BEB-C | 4.0% |
| 3-BEB-C | 12.0% |
| 3-DB-C | 10.0% |
| 4-DB-C | 10.0% |
| 3-HEB-04 | 8.0% |
| 4-HEB-02 | 6.0% |
| 5-HEB-01 | 6.0% |
| 3-HEB-02 | 5.0% |
| 5-HEB-02 | 4.0% |
| 3-HHB-1 | 6.0% |
| 3-HHEBB-C | 3.0% |
| 3-HBEBB-C | 3.0% |

-continued

| 10-BEB-2 | 5.0% |
|---|---|
| 4-HEB-3 | 3.0% |
| 5-HEB-1 | 3.0% |
| 6-PyB-02 | 3.0% |
| Use Example 7 | |
| V2-HH-VFF (No. 25) | 4.0% |
| 1V-BHH-VFF (No. 19) | 3.0% |
| 3-HB-C | 20.0% |
| 3-HHB-1 | 7.0% |
| 3-HHB-3 | 8.0% |
| 5-HEB-F | 3.0% |
| 7-HEB-F | 3.0% |
| 3-HHEB-F | 1.0% |
| 5-HHEB-F | 1.0% |
| 3-HEB-04 | 4.0% |
| 4-HEB-02 | 3.0% |
| 5-HEB-01 | 3.0% |
| 3-HEB-02 | 2.5% |
| 5-HEB-02 | 2.0% |
| 3-HB(F)TB-2 | 4.0% |
| 3-HB(F)TB-3 | 4.0% |
| 3-HB(F)VB-4 | 3.0% |
| 3-H2BTB-2 | 3.0% |
| 3-H2BTB-3 | 3.0% |
| 3-H2BTB-4 | 3.0% |
| 5-HHEBB-C | 2.0% |
| 3-HBEBB-C | 3.0% |
| 5-HBEBB-C | 3.0% |
| 3-HEBEB-F | 3.0% |
| 3-HH-EMe | 2.5% |
| 101-HBBH-3 | 2.0% |
| Use Example 8 | |
| V-BHH-2VFF (No. 8) | 6.0% |
| 5-PyB(F)-F | 13.0% |
| 2-HB(F)-C | 10.0% |
| 3-HB(F)-C | 12.0% |
| 30-BB-C | 8.0% |
| 2-HHB-C | 6.0% |
| 3-HHB-C | 6.0% |
| 4-HHB-C | 6.0% |
| 2-HHB(F)-C | 5.0% |
| 3-HHB(F)-C | 5.0% |
| 3-PyBB-F | 7.0% |
| 4-PyBB-F | 6.0% |
| 5-HBB-C | 5.0% |
| 3-HB(F)EB(F)-C | 5.0% |
| Use Example 9 | |
| V2-HH-VFF (No. 25) | 10.0% |
| 2-BEB(F)-C | 5.0% |
| 3-BEB(F)-C | 7.0% |
| 4-BEB(F)-C | 5.0% |
| 5-BEB(F)-C | 7.0% |
| 103-HB(F)-C | 6.0% |
| 3-HHEB(F)-F | 5.0% |
| 4-HHEB(F)-F | 5.0% |
| 5-HHEB(F)-F | 10.0% |
| 2-HBEB(F)-C | 5.0% |
| 3-HBEB(F)-C | 5.0% |
| 4-HBEB(F)-C | 5.0% |
| 5-HBEB(F)-C | 5.0% |
| 3-HBTB-2 | 10.0% |
| V2-HH-3 | 5.0% |
| V2-HHB-1 | 5.0% |
| Use Example 10 | |
| V2-HH-VFF (No. 25) | 15.0% |
| 1V2-BH-VFF (No. 117) | 5.0% |
| V2-HB-C | 3.0% |
| 4-BB-2 | 5.0% |
| 3-BB-C | 5.0% |
| 5-BB-C | 5.0% |
| 2-HB(F)-C | 5.0% |
| 3-H2B-02 | 5.0% |
| 5-H2B-03 | 10.0% |
| 3-BEB-C | 5.0% |
| 5-HEB-01 | 6.0% |

|  |  |
|---|---|
| 5-HEB-03 | 6.0% |
| 5-BBB-C | 3.0% |
| 4-BPyB-C | 3.0% |
| 4-BPyB-5 | 3.0% |
| 5-HB2B-4 | 4.0% |
| 5-HBB2B-3 | 4.0% |
| V2-HH-101 | 3.0% |
| 1V2-HBB-3 | 5.0% |
| Use Example 11 | |
| V2-HH-VFF (No. 25) | 5.0% |
| V-HH-VFF (No. 1) | 5.0% |
| 5-H2B(F)-F | 4.0% |
| 7-HB(F)-F | 10.0% |
| 2-HHB(F)-F | 12.0% |
| 3-HHB(F)-F | 12.0% |
| 5-HHB(F)-F | 12.0% |
| 2-H2HB(F)-F | 12.0% |
| 3-H2HB(F)-F | 6.0% |
| 5-H2HB(F)-F | 12.0% |
| 2-HBB(F)-F | 2.5% |
| 3-HBB(F)-F | 2.5% |
| 5-HBB(F)-F | 5.0% |
| Use Example 12 | |
| V2-HH-VFF (No. 25) | 7.0% |
| 7-HB(F,F)-F | 2.0% |
| 2-HHB(F)-F | 10.0% |
| 3-HHB(F)-F | 14.0% |
| 5-HHB(F)-F | 14.0% |
| 2-H2HB(F)-F | 4.0% |
| 3-H2HB(F)-F | 2.0% |
| 5-H2HB(F)-F | 4.0% |
| 3-HHB(F,F)-F | 8.0% |
| 4-HHB(F,F)-F | 4.0% |
| 3-H2HB(F,F)-F | 6.0% |
| 4-H2HB(F,F)-F | 5.0% |
| 5-H2HB(F,F)-F | 5.0% |
| 3-HH2B(F,F)-F | 8.0% |
| 5-HH2B(F,F)-F | 7.0% |
| Use Example 13 | |
| 1V2-HHH-VFF (No. 41) | 8.0% |
| 7-HB(F,F)-F | 5.0% |
| 3-HBB(F,F)-F | 5.0% |
| 5-HBB(F,F)-F | 5.0% |
| 3-HHB(F,F)-F | 7.0% |
| 5-HHB(F,F)-F | 5.0% |
| 3-HH2B(F,F)-F | 8.0% |
| 5-HH2B(F,F)-F | 5.0% |
| 3-H2HB(F,F)-F | 10.0% |
| 4-H2HB(F,F)-F | 10.0% |
| 5-H2HB(F,F)-F | 10.0% |
| 3-HHEB(F,F)-F | 8.0% |
| 4-HHEB(F,F)-F | 3.0% |
| 5-HHEB(F,F)-F | 3.0% |
| 3-HBEB(F,F)-F | 2.0% |
| 5-HBEB(F,F)-F | 2.0% |
| 3-HHHB(F,F)-F | 2.0% |
| 5-HH2BB(F,F)-F | 2.0% |
| Use Example 14 | |
| 1V2-BH-VFF (No. 117) | 5.0% |
| V2-BH-VFF (No. 27) | 5.0% |
| 5-HB-F | 2.0% |
| 7-HB(F)-F | 3.0% |
| 2-HHB(F)-F | 14.0% |
| 3-HHB(F)-F | 14.0% |
| 5-HHB(F)-F | 14.0% |
| 3-HB-02 | 5.0% |
| 3-HHB-F | 4.0% |
| 3-HHB-1 | 6.0% |
| 3-HHB-3 | 6.0% |
| 2-HBB-F | 6.0% |
| 3-HBB-F | 5.0% |
| 3-HHEB-F | 3.0% |
| 5-HHEB-F | 3.0% |
| 3-HBEB-F | 3.0% |
| 3-HHEBB-F | 2.0% |

|  |  |
|---|---|
| Use Example 15 | |
| V2-HH-VFF (No. 25) | 5.0% |
| 1V2-BHH-VFF (No. 118) | 3.0% |
| 7-HB(F,F)-F | 7.0% |
| 3-HB-CL | 5.0% |
| 7-HB-CL | 5.0% |
| 2-BTB-01 | 10.0% |
| 2-HBB(F)-F | 2.5% |
| 3-HBB(F)-F | 2.5% |
| 5-HBB(F)-F | 5.0% |
| 3-HBB(F,F)-F | 7.0% |
| 5-HBB(F,F)-F | 10.0% |
| 2-HHB-CL | 5.0% |
| 3-HHB-CL | 3.0% |
| 3-HB(F)TB-2 | 6.0% |
| 3-HB(F)TB-4 | 6.0% |
| 2-H2BTB-2 | 4.0% |
| 2-H2BTB-3 | 4.0% |
| 3-H2BB(F)-CL | 4.0% |
| 5-H2BB(F)-CL | 3.0% |
| 3-H2BB(F,F)-F | 3.0% |
| Use Example 16 | |
| V2-HH-VFF (No. 25) | 5.0% |
| 1V2-BH-VFF (No. 117) | 5.0% |
| 5-HB-F | 10.0% |
| 6-HB-F | 5.0% |
| 7-HB-F | 5.0% |
| 2-HHB-OCF3 | 5.0% |
| 3-HHB-OCF3 | 5.0% |
| 5-HHB-OCF3 | 5.0% |
| 3-HH2B-OCF3 | 6.0% |
| 5-HH2B-OCF3 | 6.0% |
| 3-HB(F)B-3 | 4.0% |
| 5-HB(F)B-3 | 4.0% |
| 2-HBB(F)-F | 10.0% |
| 3-HBB(F)-F | 10.0% |
| 5-HBB(F)-F | 15.0% |
| Use Example 17 | |
| V2-HH-VFF (No. 25) | 6.0% |
| V-HH-2VFF (No. 116) | 3.0% |
| 1V2-HH-VFF (No. 37) | 3.0% |
| 5-HB-F | 3.0% |
| 6-HB-F | 3.0% |
| 7-HB-F | 3.0% |
| 3-HHB-OCF2H | 7.0% |
| 5-HHB-OCF2H | 7.0% |
| 3-HHB(F,F)-OCF2H | 9.0% |
| 5-HHB(F,F)-OCF2H | 9.0% |
| 2-HHB-OCF3 | 6.0% |
| 3-HHB-OCF3 | 6.0% |
| 4-HHB-OCF3 | 6.0% |
| 5-HHB-OCF3 | 6.0% |
| 3-HH2B(F)-F | 7.0% |
| 5-HH2B(F)-F | 7.0% |
| 3-HHEB(F)-F | 4.0% |
| 5-HHEB(F)-F | 5.0% |
| Use Example 18 | |
| V2-HH-VFF (No. 25) | 15.0% |
| 3-HEB-04 | 23.4% |
| 4-HEB-02 | 17.6% |
| 5-HEB-01 | 17.6% |
| 3-HEB-02 | 14.7% |
| 5-HEB-02 | 11.7% |
| $T_{NI} = 67.7$ (° C.) | |
| $\eta = 19.6$ (mPa · s) | |
| Use Example 19 | |
| V2-HHH-VFF (No. 29) | 15.0% |
| 3-HEB-04 | 23.4% |
| 4-HEB-02 | 17.6% |
| 5-HEB-01 | 17.6% |
| 3-HEB-02 | 14.7% |
| 5-HEB-02 | 11.7% |
| $T_{NI} = 89.6$ (° C.) | |
| $\eta = 25.7$ (mPa · s) | |

-continued

Use Example 20

| | |
|---|---|
| V2-HH-2VFF (No. 115) | 15.0% |
| 3-HEB-04 | 23.4% |
| 4-HEB-02 | 17.6% |
| 5-HEB-01 | 17.6% |
| 3-HEB-02 | 14.7% |
| 5-HEB-02 | 11.7% |

$T_{NI} = 69.5$ (° C.)
$\eta = 20.5$ (mPa · s)

Use Example 21

| | |
|---|---|
| V2-HH-VFF (No. 25) | 10.0% |
| V2-HH-2VFF (No. 115) | 8.0% |
| 1V2-BEB(F,F)-C | 5.0% |
| 3-HB-C | 25.0% |
| 1-BTB-3 | 5.0% |
| 3-HH-4 | 3.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

$T_{NI} = 93.3$ (° C.)
$\eta = 13.9$ (mPa · s)
$\Delta n = 0.147$
$V_{th} = 2.08$ (V)

When 0.8 parts of CM33 was added to 100 parts of the above-mentioned composition, pitch was 10.5 μm.

Use Example 22

| | |
|---|---|
| V2-HHH-VFF (No. 29) | 8.0% |
| 201-BEB(F)-C | 5.0% |
| 301-BEB(F)-C | 15.0% |
| 401-BEB(F)-C | 13.0% |
| 501-BEB(F)-C | 13.0% |
| 2-HHB(F)-C | 15.0% |
| 3-HHB(F)-C | 15.0% |
| 3-HB(F)TB-2 | 4.0% |
| 3-HB(F)TB-3 | 4.0% |
| 3-HB(F)TB-4 | 4.0% |
| 3-HHB-01 | 4.0% |

$T_{NI} = 94.5$ (° C.)
$\eta = 85.5$ (mPa · s)
$\Delta n = 0.149$
$V_{th} = 0.90$ (V)

Use Example 23

| | |
|---|---|
| V2-HH-VFF (No. 25) | 4.0% |
| V2-HH-2VFF (No. 115) | 9.0% |
| V2-HHH-VFF (No. 29) | 8.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 6-PyB-05 | 3.0% |
| 3-PyBB-F | 6.0% |
| 4-PyBB-F | 6.0% |
| 5-PyBB-F | 6.0% |
| 3-HHB-1 | 6.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

$T_{NI} = 99.4$ (° C.)
$\eta = 28.5$ (mPa · s)
$\Delta n = 0.191$
$V_{th} = 2.32$ (V)

Use Example 24

| | |
|---|---|
| V2-HH-VFF (No. 25) | 25.0% |
| 3-DB-C | 10.0% |
| 4-DB-C | 10.0% |

-continued

| | |
|---|---|
| 2-BEB-C | 12.0% |
| 3-BEB-C | 4.0% |
| 3-PyB(F)-F | 6.0% |
| 5-HEB-02 | 4.0% |
| 5-HEB-5 | 5.0% |
| 4-HEB-5 | 5.0% |
| 10-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

$T_{NI} = 67.3$ (° C.)
$\eta = 31.0$ (mPa · s)
$\Delta n = 0.121$
$V_{th} = 1.28$ (V)

Use Example 25

| | |
|---|---|
| V2-HH-2VFF (No. 115) | 4.0% |
| 3-HB-C | 18.0% |
| 7-HB-C | 3.0% |
| 101-HB-C | 10.0% |
| 3-HB(F)-C | 10.0% |
| 4-PyB-2 | 2.0% |
| 101-HH-3 | 7.0% |
| 2-BTB-01 | 7.0% |
| 3-HHB-1 | 7.0% |
| 3-HHB-F | 4.0% |
| 3-HHB-01 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

$T_{NI} = 81.4$ (° C.)
$\eta = 16.9$ (mPa · s)
$\Delta n = 0.137$
$V_{th} = 1.77$ (V)

Use Example 26

| | |
|---|---|
| 1V2-HH-VFF (No. 37) | 5.0% |
| 1V2-HH-2VFF (No. 38) | 8.0% |
| 201-BEB(F)-C | 5.0% |
| 301-BEB(F)-C | 12.0% |
| 501-BEB(F)-C | 4.0% |
| 1V2-BEB(F,F)-C | 10.0% |
| 3-HH-EMe | 5.0% |
| 3-HB-02 | 10.0% |
| 7-HEB-F | 2.0% |
| 3-HHEB-F | 2.0% |
| 5-HHEB-F | 2.0% |
| 3-HBEB-F | 4.0% |
| 201-HBEB(F)-C | 2.0% |
| 3-HB(F)EB-C | 2.0% |
| 3-HBEB(F,F)-C | 2.0% |
| 3-HHB-F | 4.0% |
| 3-HHB-01 | 4.0% |
| 3-HHB-3 | 13.0% |
| 3-HEBEB-F | 2.0% |
| 3-HEBEB-1 | 2.0% |

Use Example 27

| | |
|---|---|
| 1V-HH-VFF (No. 13) | 5.0% |
| 1V-HH-2VFF (No. 14) | 5.0% |
| V2-HHH-VFF (No. 29) | 8.0% |
| 201-BEB(F)-C | 5.0% |
| 301-BEB(F)-C | 12.0% |
| 501-BEB(F)-C | 4.0% |
| 1V2-BEB(F,F)-C | 16.0% |
| 3-HH-4 | 3.0% |
| 3-HHB-F | 3.0% |
| 3-HHB-01 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |

Use Example 28

| | |
|---|---|
| V2-HH-VFF (No. 25) | 20.0% |
| V2-HHH-VFF (No. 29) | 4.0% |
| 2-BEB-C | 12.0% |
| 3-BEB-C | 4.0% |
| 4-BEB-C | 6.0% |
| 3-HB-C | 28.0% |
| 5-HEB-01 | 8.0% |
| 3-HEB-02 | 6.0% |
| 5-HEB-02 | 5.0% |
| 3-HHB-1 | 7.0% |

$T_{NI}$ = 60.4 (° C.)
$\eta$ = 18.2 (mPa · s)
$\Delta n$ = 0.112
$V_{th}$ = 1.31 (V)

Use Example 29

| | |
|---|---|
| 1V2-HH-VFF (No. 37) | 5.0% |
| 1V-HH-VFF (No. 13) | 5.0% |
| 1V2-HH-2VFF (No. 38) | 5.0% |
| 1V-HH-2VFF (No. 14) | 5.0% |
| 2-BEB-C | 10.0% |
| 5-BB-C | 12.0% |
| 7-BB-C | 7.0% |
| 1-BTB-3 | 7.0% |
| 10-BEB-5 | 12.0% |
| 2-HHB-1 | 4.0% |
| 3-HHB-F | 4.0% |
| 3-HHB-1 | 7.0% |
| 3-HHB-01 | 4.0% |
| 3-HHB-3 | 13.0% |

Use Example 30

| | |
|---|---|
| V2-HH-2VFF (No. 115) | 20.0% |
| 1V2-BEB(F,F)C | 6.0% |
| 3-HB-C | 18.0% |
| 2-BTB-1 | 10.0% |
| 5-HH-VFF | 10.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |
| 3-HHB-1 | 4.0% |

$T_{NI}$ = 83.1 (° C.)
$\eta$ = 11.7 (mPa · s)
$\Delta n$ = 0.132
$V_{th}$ = 2.10 (V)

Use Example 31

| | |
|---|---|
| V2-HHH-VFF (No. 29) | 8.0% |
| 2-HB-C | 5.0% |
| 3-HB-C | 12.0% |
| 3-HB-02 | 15.0% |
| 2-BTB-1 | 3.0% |
| 3-HHB-F | 4.0% |
| 3-HHB-01 | 5.0% |
| 3-HHB-3 | 14.0% |
| 3-HHEB-F | 4.0% |
| 5-HHEB-F | 4.0% |
| 2-HHB(F)-F | 7.0% |
| 3-HHB(F)-F | 7.0% |
| 5-HHB(F)-F | 7.0% |
| 3-HHB(F,F)-F | 5.0% |

$T_{NI}$ = 103.0 (° C.)
$\eta$ = 17.2 (mPa · s)
$\Delta n$ = 0.099
$V_{th}$ = 2.56 (V)

Use Example 32

| | |
|---|---|
| V2-HH-VFF (No. 25) | 3.0% |
| V2-HHH-VFF (No. 29) | 5.0% |
| 3-BEB(F)-C | 8.0% |
| 3-HB-C | 8.0% |
| V-HB-C | 8.0% |
| 1V-HB-C | 8.0% |
| 3-HH-2V | 14.0% |
| 3-HH-2V1 | 7.0% |
| V2-HHB-1 | 15.0% |
| 3-HHEB-F | 7.0% |
| 3-H2BTB-2 | 6.0% |
| 3-H2BTB-3 | 6.0% |
| 3-H2BTB-4 | 5.0% |

$T_{NI}$ = 101.3 (° C.)
$\eta$ = 15.2 (mPa · s)
$\Delta n$ = 0.132
$V_{th}$ = 2.25 (V)

Use Example 33

| | |
|---|---|
| V2-HH-2VFF (No. 115) | 31.0% |
| 1V2-BEB(F,F)-C | 12.0% |
| 3-HB-C | 4.0% |
| 3-HB-02 | 5.5% |
| 3-HHB-1 | 3.5% |
| 1-BHH-VFF | 20.0% |
| 3-HB(F)TB-2 | 4.0% |
| 3-HB(F)TB-3 | 4.0% |
| 3-HB(F)TB-4 | 4.0% |
| 3-H2BTB-2 | 4.0% |
| 3-H2BTB-3 | 4.0% |
| 3-H2BTB-4 | 4.0% |

$T_{NI}$ = 100.4 (° C.)
$\eta$ = 14.1 (mPa · s)
$\Delta n$ = 0.133
$V_{th}$ = 2.16 (V)

When 2.0 parts of CN was added to 100 parts of the above-mentioned composition, pitch was 10.6 μm.

Use Example 34

| | |
|---|---|
| V2-HH-VFF (No. 25) | 28.0% |
| 1V2-BEB(F,F)-C | 12.0% |
| 3-HB-C | 4.0% |
| 3-HB-02 | 5.5% |
| 3-HHB-1 | 8.5% |
| 1-BHH-VFF | 20.0% |
| 3-HB(F)TB-2 | 5.0% |
| 3-HB(F)TB-3 | 5.0% |
| 3-H2BTB-2 | 4.0% |
| 3-H2BTB-3 | 4.0% |
| 3-H2BTB-4 | 4.0% |

$T_{NI}$ = 100.5 (° C.)
$\eta$ = 13.9 (mPa · s)
$\Delta n$ = 0.132
$V_{th}$ = 2.14 (V)

When 1.81 parts of CN was added to 100 parts of the above-mentioned composition, pitch was 12.3 μm.

Use Example 35

| | |
|---|---|
| V2-HH-VFF (No. 25) | 15.0% |
| 201-BEB(F)-F | 10.0% |
| 301-BEB(F)-F | 26.0% |
| 1V2-BEB(F,F)-C | 5.0% |
| 2-HHB(F)-C | 14.0% |
| 3-HHB(F)-C | 14.0% |
| 3-HB(F)TB-2 | 5.0% |
| 3-HB(F)TB-3 | 5.0% |
| 3-HHB-1 | 6.0% |

$T_{NI}$ = 85.3 (° C.)
$\eta$ = 51.1 (mPa · s)
$\Delta n$ = 0.143
$V_{th}$ = 0.96 (V)

Use Example 36

| | |
|---|---|
| V2-HH-VFF (No. 25) | 8.0% |
| 2-HBEB(F,F)-F | 3.0% |
| 3-HBEB(F,F)-F | 5.0% |
| 5-HBEB(F,F)-F | 3.0% |
| 3-HB-C | 20.0% |
| 1V2-BEB(F,F)-C | 30.0% |
| 3-HHB-3 | 10.0% |
| 3-HHB-01 | 5.0% |
| 3-HHEB-F | 3.0% |
| 5-HHEB-F | 3.0% |
| 3-H2BTB-2 | 5.0% |

-continued

| 3-H2BTB-3 | 5.0% |
|---|---|
| $T_{NI}$ = 77.0 (° C.) | |
| η = 34.0 (mPa · s) | |
| Δn = 0.137 | |
| $V_{th}$ = 0.98 (V) | |

Preparation of Compounds

Compounds (1) of the present invention can be prepared easily by utilizing conventional organic synthetic chemical methods. They can be synthesized easily by selecting and combining appropriately known reactions described for example in books such as Organic Synthesis, Organic Reactions, Shin Zikken Kagaku Koza, and magazines.

That is, a liquid crystalline compound of the present invention can be prepared by reacting a triphenyl phosphonium halide derivative (12) with an aldehyde derivative (11) in an ether solvent such as THF and diethyl ether etc. in the presence of a base such as sodium methylate, potassium-t-butoxide (t-BuOK) and butyl lithium etc. to obtain (13) according to the known method which utilizes Wittig reaction such as method described in Organic Reactions, Vol.14, Chapter 3 etc., reacting diisobutyl aluminium halide (hereinafter abbreviated as DIBAL) with (13) in toluene to obtain an aldehyde derivative (14), and then reacting (15) and triphenylphosphine with (14) to prepare the compound (1) of the present invention.

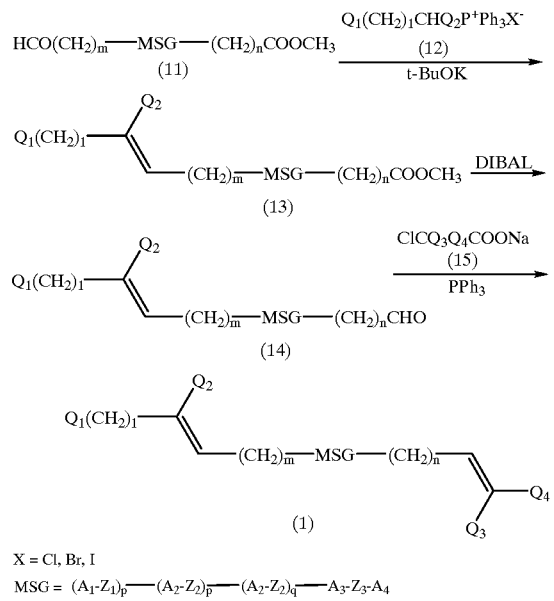

X = Cl, Br, I
MSG = (A₁-Z₁)ₚ—(A₂-Z₂)ₚ—(A₂-Z₂)q—A₃-Z₃-A₄

Furthermore, in the case of $Q_1=Q_2 \neq H$ and $l=0$, the following method is preferable. That is, compound (1) of the present invention can be prepared by reacting an aldehyde derivative (11) with (16) and triphenylphosphine in N,N-dimethyl formamide (hereinafter abbreviated as DMF) to obtain (17), and treating it by the same series of the above-mentioned operations for obtaining (1) from (13).

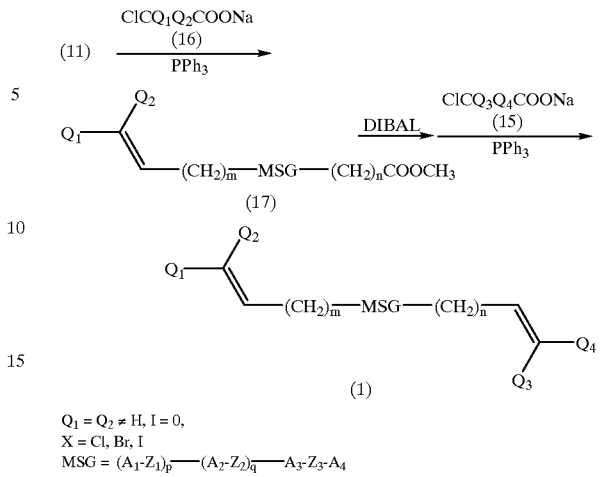

$Q_1 = Q_2 \neq H$, $I = 0$,
X = Cl, Br, I
MSG = (A₁-Z₁)ₚ—(A₂-Z₂)q—A₃-Z₃-A₄

Furthermore, compounds in which $A_1$, $A_2$, $A_3$ and $A_4$ being silacyclohexane ring can be prepared according to methods disclosed in Toku-Kai-Hei 7-70148, Toku-Kai-Hei 7-112990 and Toku-Kai-Hei 7-149770.

Liquid crystalline compounds of the invention thus obtained show wide liquid crystal phase temperature ranges, are low viscous, have high elastic constant ratios $K_{33}/K_{11}$, are mixed easily with other various liquid crystal materials even at lower temperatures, and also are quite superior as constitution components of nematic liquid crystal compositions suitable for a STN type display method.

EXAMPLES

The invention is explained in more detail by the following examples, but the invention is not restricted by these examples. Herein, constitutions of compounds were confirmed by nuclear magnetic resonance spectrum (hereinafter abbreviated as 1H-NMR) and mass spectrum (hereinafter abbreviated as MS) etc. In examples, d denotes doublet, t denotes triplet, m denotes multiplet, and J denotes a coupling constant in NMR. M+ denotes a molecular ion peak and values in parentheses denote an ion strength in MS. Cr denotes a cryatal phase, S denotes a smetic phase, N denotes a nematic phase, Iso denotes an isotropic liquid phase and phase transfer temperature units are all ° C.

Example 1

Preparation of 1-(2,2-difluoroethenyl)-trans-4-(trans-4-(3-butenyl)cyclohexyl)cyclohexane (compound (No. 25) of the formula (1) in which $A_3$ and $A_4$ are trans-1,4-cyclohexylene groups; $Z_3$ is a covalent bond; $Q_1$ and $Q_2$ are H; $Q_3$ and $Q_4$ are F; l, n, p and q are 0; and m is 2)

The first step

A mixture of 165.6 g (463.6 mmol) of methyl triphenyl phosphonium bromide and 1.5 liters of THF was cooled to −50° C. under a gas stream of nitrogen. To the mixture, 57.2 g (509.8 mmol) of t-BuOK was added and stirred for 1 hour. To the mixture, a solution of 100.0 g (356.6 mmol) of methyl trans-4-(trans-4-(2-formylethyl)cyclohexyl)cyclohexane carboxylate in 1 liter of THF was added dropwise with maintaining the temperature below −50° C. After dropwise addition, the reaction temperature was increased gradually to the room temperature, and stirring was carried out further for 5 hours. The solvent was distilled off under a decreased pressure, then 500 ml of water was added and the mixture was extracted with 500 ml of toluene. The organic layer was washed with 200 ml of water for three times and dried with anhydrous magnesium sulphate.

The solvent was distilled off under a decreased pressure, and the residue was subjected to silica gel column chromatography (eluent: a mixed solvent of ethyl acetate/heptane= 1/10), to obtain 34.8 g of crude methyl trans-4-(trans-4-(3-butenyl)cyclohexyl)cyclohexane carboxylate.

The second step 34.8 g (125.0 mmol) of the crude product was dissolved in 500 ml of toluene, to which 125 ml of 1.0M solution of DIBAL in toluene was added dropwise under a gas stream of nitrogen with maintaining the temperature below −50° C. After stirring at the same temperature for 1 hour, the reaction was ended by pouring the reaction solution gradually into water. It was washed with 300 ml of water for three times and dried with anhydrous magnesium sulphate. The solvent was distilled off under a decreased pressure, to obtain 30.3 g of crude trans-4-(trans-4-(3-butenyl)cyclohexyl) cyclohexane carbaldehyde.

The third step 30.3 g (122.0 mmol) of crude trans-4-(trans-4-(3-butenyl)cyclohexyl)cyclohexane carbaldehyde and 41.6 g (158.6 mmol) of triphenylphosphine were added to 600 ml of a mixed solvent of toluene/DMF (1/5) with stirring under a gas flow of nitrogen, the temperature of which being increased. Once the temperature becoming 100~110° C., a solution of 37.2 g (244.0 mmol) of sodium chlorodifluoroacetate in 400 ml of DMF was added dropwise with maintaining the same temperature. After completion of dropwise addition, it was stirred for 30 minutes and allowed to cool to the room temperature. 1 liter of water and 1 liter of heptane were added to the reaction mixture, stirred thoroughly, and thereafter filtered with Celite. Then, the water layer was extracted with 500 ml of heptane, the organic layer was washed with 700 ml of water for three times and dried with anhydrous magnesium sulphate.

The solvent was distilled off under a decreased pressure and the residue was subjected to silica gel column chromatograpy (eluent: heptane), to obtain 13.3 g of crude 1-(2,2-difluoroethenyl)-trans-4-(trans-4-(3-butenyl) cyclohexyl) cyclohexane. The crude product was recrystallized from Solmix, to obtain 13.3 g of the title compound (yield 13.2%).

Phase transfer temperature: Cr −7.1 S −4.9 N 49.7 Iso
$^1$H-NMR: δ: (ppm) : 0.50~2.38 (m, 24H), 3.99 (d, d, d, 1H, $J_{H-F}$=22.9, 9.2, J=6.3), 4.80~5.15 (m, 2H), 5.82 (d, d, t, 1H, $J_{H-F}$=17.2, 10.0, J=6.7), MS:m/e=282(M$^+$), 225, 211, 135, 95, 81, 67.

Example 2

Preparation of 1-(4,4-difluoro-3-butenyl)-trans-4-(trans-4-(trans-4-ethenylcyclohexyl)cyclohexyl)cyclohexane (compound (No. 6) of the formula (1) in which $A_2$, $A_3$ and $A_4$ are trans-1,4-cyclohexylene groups; $Z_2$ and $Z_3$ are covalent bonds; $Q_1$ and $Q_2$ are H; $Q_3$ and $Q_4$ are F; 1, m and p are 0; q is 1; and n is 2)

The first step

A mixture of 128.1 g (358.6 mmol) of methyl triphenyl phosphonium bromide and 1.5 liters of THF was cooled to −50° C. under a gas stream of nitrogen. To the mixture, 44.3 g (394.8 mmol) of t-BuOK was added and stirred for 1 hour. To the mixture, a solution of 100.0 g (275.8 mmol) of methyl 2-(trans-4-(trans-4-(trans-4-formylcyclohexyl)cyclohexyl) cyclohexyl)ethane carboxylate in 1 liter of THF was added dropwise with maintaining the temperature below −50° C. After dropwise addition, the reaction temperature was increased gradually to the room temperature, and stirring was carried out further for 5 hours. The solvent was distilled off under a decresed pressure, 500 ml of water was added and the mixture was extracted with 500 ml of toluene. The organic layer was washed with 200 ml of water for three times and dried with anhydrous magnesium sulphate.

The solvent was distilled off under a decreased pressure, and the residue was subjected to silica gel column chromatography (eluent: a mixed solvent of ethyl acetate/heptane= 1/8), to obtain 37.8 g of crude methyl 2-(trans-4-(trans-4-(trans-4-ethenylcyclohexyl)cyclohexyl)cyclohexyl)ethane carboxylate.

The second step 37.8 g (104.8 mmol) of the crude product was dissolved in 500 ml of toluene, to which 105 ml of 1.0M solution of DIBAL in toluene was added dropwise under a gas stream of nitrogen with maintaining the temperature below −50° C. After stirring at the same temperature for 1 hour, the reaction was ended by pouring the reaction solution gradually into water. It was washed with 300 ml of water for three times and dried with anhydrous magnesium sulphate. The solvent was distilled off under a decreased pressure, to obtain 32.9 g of crude 3-(trans-4-(trans-4-(trans-4-ethenylcyclohexyl) cyclohexyl)cyclohexyl)propanal.

The third step 32.9 g (99.5 mmol) of crude 3-(trans-4-(trans-4-(trans-4-ethenylcyclohexyl)cyclohexyl)cyclohexyl)propanal and 33.9 g (129.2 mmol) of triphenylphosphine were added to 600 ml of a mixed solvent of toluene/DMF (1/5) with stirring under a gas flow of nitrogen, the temperature of which being increased. Once the temperature becoming 100~110° C., a solution of 30.3 g (198.7 mmol) of sodium chlorodifluoroacetate in 300 ml of DMF was added dropwise with maintaining the same temperature. After completion of dropwise addition, it was stirred for 30 minutes and allowed to cool to the room temperature. 1 liter of water and 1 liter of heptane were added to the reaction mixture, stirred thoroughly, and thereafter filtered with Celite. Then, the water layer was extracted with 500 ml of heptane, the organic layer was washed with 700 ml of water for three times and dried with anhydrous magnesium sulphate.

The solvent was distilled off under a decreased pressure and the residue was subjected to silica gel column chromatograpy (eluent: heptane), to obtain crude 1-(4,4-difluoro-3-butenyl)-trans-4-(trans-4-(trans-4-ethenylcyclohexyl)cyclohexyl) cyclohexane. The crude product was recrystallized from Solmix, to obtain 14.5 g of the title compound (yield 14.4%).

MS:m/e=364 (M$^+$).

Example 3

Preparation of 1-(2,2-difluoroethenyl)-trans-4-(trans-4-(4-(3-butenyl)phenyl)cyclohexyl)cyclohexane (compound (No. 31) of the formula (1) in which $A_2$ is 1,4-phenylene group; rings $A_3$ and $A_4$ are trans-1,4-cyclohexylene groups; $Z_2$ and $Z_3$ are covalent bonds; $Q_1$ and $Q_2$ are H; $Q_3$ and $Q_4$ are F; 1, n and p are 0; q is 1; and m is 2)

The first step

A mixture of 130.3 g (364.8 mmol) of methyl triphenyl phosphonium bromide and 1.5 liters of THF was cooled to −50° C., under a gas stream of nitrogen. To the mixture, 45.0 g (401.0 mmol) of t-BuOK was added and stirred for 1 hour. To the mixture, a solution of 100.0 g (280.5 mmol) of methyl trans-4-(trans-4-(4-(2-formylethyl)phenyl)cyclohexyl) cyclohexane carboxylate in 1 liter of THF was added dropwise with maintaining the temperature below −50° C. After dropwise addition, the reaction temperature was increased gradually to the room temperature, and stirring was carried out further for 5 hours.

The solvent was distilled off under a decreased pressure, then 500 ml of water was added and the mixture was extracted with 500 ml of toluene. The organic layer was washed with 200 ml of water for three times and dried with anhydrous magnesium sulphate. The solvent was distilled off under a decreased pressure, and the residue was subjected to silica gel column chromatography (eluent: a mixed solvent of ethyl acetate/heptane=1/8), to obtain 37.8 g of crude methyl trans-4-(trans-4-(4-(3-butenyl)phenyl) cyclohexyl)cyclohexane carboxylate.

The second step 37.8 g (106.6 mmol) of the crude product was dissolved in 500 ml of toluene, to which 107 ml of 1.0M solution of DIBAL in toluene was added dropwise under a gas stream of nitrogen with maintaining the temperature below −50° C. After stirring at the same temperature for 1 hour, the reaction was ended by pouring the reaction solution gradually into water. It was washed with 300 ml of water for three times and dried with anhydrous magnesium sulphate. The solvent was distilled off under a decreased pressure, to obtain 31.8 g of crude trans-4-(trans-4-(4-(3-butenyl)phenyl) cyclohexyl)cyclohexane carbaldehyde.

The third step 31.8 g (98.0 mmol) of crude trans-4-(trans-4-(4-(3-butenyl)phenyl)cyclohexyl)cyclohexane carbaldehyde and 33.4 g (127.3 mmol) of triphenylphosphine were added to 600 ml of a mixed solvent of toluene/DMF (1/5) with stirring under a gas flow of nitrogen, the temperature of which being increased. Once the temperature becoming 100~110° C., a solution of 29.9 g (196.1 mmol) of sodium chlorodifluoroacetate in 300 ml of DMF was added dropwise with maintaining the same temperature. After completion of dropwise addition, it was stirred for 30 minutes and allowed to cool to the room temperature. 1 liter of water and 1 liter of heptane were added to the reaction mixture, stirred thoroughly, and thereafter filtered with Celite. Then, the water layer was extracted with 500 ml of heptane, the organic layer was washed with 700 ml of water for three times and dried with anhydrous magnesium sulphate.

The solvent was distilled off under a decreased pressure and the residue was subjected to silica gel column chromatograpy (eluent: heptane), to obtain crude 1-(2,2-difluoroethenyl)-trans-4- (trans-4- (4- (3-butenyl) phenyl) cyclohexyl) cyclohexane. The crude product was recrystallized from Solmix, to obtain 14.4 g of the title compound (yield 14.3%).

MS:m/e=358(M+).

Example 4

Preparation of 1-(2,2-difluoroethenyl)-trans-4-(4-(4-trans-4-(3-butenyl)cyclohexyl)phenyl)phenyl)cyclohexane (compound (No. 35) of the formula (1) in which $A_1$ and $A_4$ are trans-1,4-cyclohexylene groups; $A_2$ and $A_3$ are 1,4-phenylene groups; $Z_1$, $Z_2$ and $Z_3$ are covalent bonds; $Q_1$ and $Q_2$ are H; $Q_3$ and $Q_4$ are F; 1 and n are 0; p and q are 1; and m is 2)

The first step

A mixture of 107.4 g (300.6 mmol) of methyl triphenyl phosphonium bromide and 1 liter of THF was cooled to −50° C. under a gas stream of nitrogen. To the mixture, 37.1 g (330.6 mmol) of t-BuOK was added and stirred for 1 hour. To the mixture, a solution of 100.0 g (231.2 mmol) of methyl trans-4-(4-(4-(trans-(2-formylethyl)cyclohexyl)phenyl) phenyl)cyclohexane carboxylate in 1 liter of THF was added dropwise with maintaining the temperature below −50° C. After dropwise addition, the reaction temperature was increased gradually to the room temperature, and stirring was carried out further for 5 hours. The solvent was distilled off under a decresed pressure, 500 ml of water was added and the mixture was extracted with 500 ml of toluene. The organic layer was washed with 200 ml of water for three times and dried with anhydrous magnesium sulphate.

The solvent was distilled off under a decreased pressure, and the residue was subjected to silica gel column chromatography (eluent: a mixed solvent of ethyl acetate/heptane= 1/7), to obtain 33.9 g of crude methyl trans-4-(4-(4-(trans-4-(3-butenyl)cyclohexyl)phenyl)phenyl)cyclohexane carboxylate.

The second step 33.9 g (78.7 mmol) of the crude product was dissolved in 350 ml of toluene, to which 79 ml of 1.0M solution of DIBAL in toluene was added dropwise under a gas stream of nitrogen with maintaining the temperature below −50° C. After stirring at the same temperature for 1 hour, the reaction was ended by pouring the reaction solution gradually into water. It was washed with 200 ml of water for three times and dried with anhydrous magnesium sulphate. The solvent was distilled off under a decreased pressure, to obtain 28.4 g of crude trans-4-(4-(4-(trans-4-(3-butenyl)cyclohexyl) phenyl)phenyl)cyclohexane carbaldehyde.

The third step 28.4 g (70.9 mmol) of crude trans-4-(4-(4-(trans-4-(3-butenyl)cyclohexyl)phenyl)phenyl)cyclohexane carbaldehyde and 24.2 g (92.3 mmol) of triphenylphosphine were added to 400 ml of a mixed solvent of toluene/DMF (1/5) with stirring under a gas flow of nitrogen, the temperature of which being increased. Once the temperature becoming 100~110° C., a solution of 21.6 g (141.7 mmol) of sodium chlorodifluoroacetate in 200 ml of DMF was added dropwise with maintaining the same temperature. After completion of dropwise addition, it was stirred for 30 minutes and allowed to cool to the room temperature. 600 ml of water and 600 ml of heptane were added to the reaction mixture, stirred thoroughly, and thereafter filtered with Celite. Then, the water layer was extracted with 300 ml of heptane, the organic layer was washed with 350 ml of water for three times and dried with anhydrous magnesium sulphate.

The solvent was distilled off under a decreased pressure and the residue was subjected to silica gel column chromatograpy (eluent: heptane), to obtain crude 1-(2,2-difluoroethenyl)-trans-4- (4- (4- (trans-4- (3-butenyl) cyclohexyl) phenyl) phenyl) cyclohexane. The crude product was recrystallized from Solmix, to obtain 13.9 g of the title compound (yield 13.8%).

MS:m/e=434(M+).

Example 5

Preparation of 1- (4,4-difluoro-3-butenyl) -trans-4-(trans-4- (3-butenyl)cyclohexyl)cyclohexane (compound (No. 115) of the formula (1) in which $A_3$ and $A_4$ are trans-1,4-cyclohexylene groups; $Z_3$ is a covalent bond; $Q_1$ and $Q_2$ are H; $Q_3$ and $Q_4$ are F; 1, p and q are 0; and m and n are 2)

The first step

A mixture of 66.4 g (193.7 mmol) of methoxymethyltriphenyl phosphonium chloride and 600 ml of THF was cooled to −50° C. under a gas stream of nitrogen. To the mixture, 20.1 g (179.1 mmol) of t-BuOK was added and stirred for 1 hour. To the mixture, a solution of 37.0 g (148.9 mmol) of trans-4-(trans-4-(3-_butenyl)cyclohexyl) cyclohexane carbaldehyde in 400 ml of THF was added dropwise with maintaining the temperature below −50° C. After dropwise addition, the reaction temperature was increased gradually to the room temperature, and stirring was carried out further for 5 hours. The solvent was distilled off under a decresed pressure, 250 ml of water was added and the mixture was extracted with 300 ml of toluene. The organic layer was washed with 200 ml of water for three times and dried with anhydrous magnesium sulphate. The solvent was distilled off under a decreased pressure, and the residue was subjected to silica gel column chromatography (eluent: a mixed solvent of toluene/heptane=3/7), to obtain 16.1 g of crude 1-(2-methoxyethenyl)-trans-4- (trans-4-(3-butenyl) cyclohexyl) cyclohexane.

The second step 16.0 g (57.9 mmol) of the crude product was dissolved in 200 ml of toluene, 30.6 g (578.3 mmol) of 87% formic acid was added and heating to reflux was carried out for 3 hours. The reaction solution was washed in order with 200 ml of water twice, 100 ml of a saturated sodium hydrogen carbonate solution for three times and 200 ml of water for three times, and then dried with anhydrous magnesium sulphate. The solvent was distilled off under a decreased pressure, to obtain 14.8 g of crude trans-4-(trans-4-(3-butenyl) cyclohexyl)cyclohexyl acetaldehyde.

The third step

A mixture of 25.2 g (73.5 mmol) of methoxymethyltriphenyl phosphonium chloride and 300 ml of THF was cooled to −50° C. under a gas stream of nitrogen. To the mixture, 7.6 g (67.8 mmol) of t-BuOK was added and stirred for 1 hour. To the mixture, a solution of 14.8 g (56.5 mmol) of trans-4-(trans-4-(3-butenyl)cyclohexyl)cyclohexyl acetaldehyde in 150 ml of THF was added dropwise with maintaining the temperature below −50° C. After dropwise addition, the reaction temperature was increased gradually to the room temperature, and stirring was carried out further for 5 hours. The solvent was distilled off under a decreased pressure, 150 ml of water was added and the mixture was extracted with 200 ml of toluene. The organic layer was washed with 100 ml of water for three times and dried with anhydrous magnesium sulphate. The solvent was distilled off under a decreased pressure, and the residue was subjected to silica gel column chromatography (eluent: a mixed solvent of toluene/heptane=3/7), to obtain 12.8 g of crude 1-(3-methoxypropenyl)-trans-4 -(trans-4-(3-butenyl) cyclohexyl)cyclohexane.

The fourth step 12.1 g (41.7 mmol) of the crude product was dissolved in 200 ml of toluene, 22.0 g (415.8 mmol) of 87% formic acid was added and heating to reflux was carried out for 3 hours. The reaction solution was washed in order with 200 ml of water twice, 100 ml of a saturated sodium hydrogen carbonate solution for three times and 200 ml of water for three times, and then dried with anhydrous magnesium sulphate. The solvent was distilled off under a decreased pressure, to obtain 11.5 g of crude trans-4-(trans-4-(3-butenyl) cyclohexyl)cyclohexyl propanal.

The fifth step 11.5 g (41.6 mmol) of crude trans-4-(trans-4-(3-butenyl) cyclohexyl)cyclohexyl propanal and 14.2 g (54.1 mmol) of triphenylphosphine were added to 100 ml of a mixed solvent of toluene/DMF (1/5) with stirring under a gas flow of nitrogen, the temperature of which being increased. Once the temperature becoming 100~110° C., a solution of 12.7 g (83.3 mmol) of sodium chlorodifluoroacetate in 100 ml of DMF was added dropwise with maintaining the same temperature. After completion of dropwise addition, it was stirred for 30 minutes and allowed to cool to the room temperature. 200 ml of water and 200 ml of heptane were added to the reaction mixture, stirred thoroughly, and thereafter filtered with Celite. Then, the water layer was extracted with 200 ml of heptane, the organic layer was washed with 300 ml of water for three times and dried with anhydrous magnesium sulphate. The solvent was distilled off under a decreased pressure and the residue was subjected to silica gel column chromatograpy (eluent: heptane), to obtain crude 1-(4,4-difluoro-3-butenyl)-trans-4-(trans-4-(3-butenyl) cyclohexyl) cyclohexane. The crude product was recrystallized from Solmix, to obtain 5.1 g of the title compound (yield 11.7%).

Phase transfer temperature: Cr −7.0 SB 49.0 N 69.0 Iso
$^1$H-NMR: δ: (ppm) : 0.40~2.55 (m, 28H), 4.10 (d, d, t, 1H, $J_{H\text{-}F}$=25.3, J=7.7, $J_{H\text{-}F}$=3.1), 4.80~5.20 (m, 2H), 5.82 (d, d, t, 1H, $J_{H\text{-}F}$=17.1, 9.9, J=6.7).

MS:m/e=310(M$^+$), 253, 239, 137, 95, 81, 67.

The following compounds can be prepared according to the methods of Examples 1 to 5.

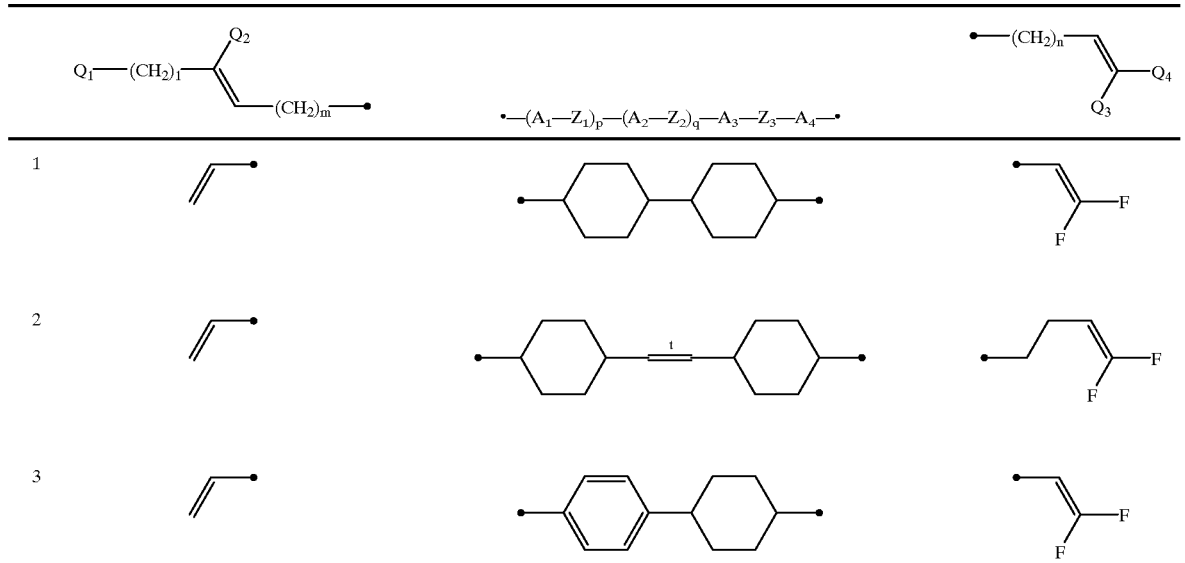

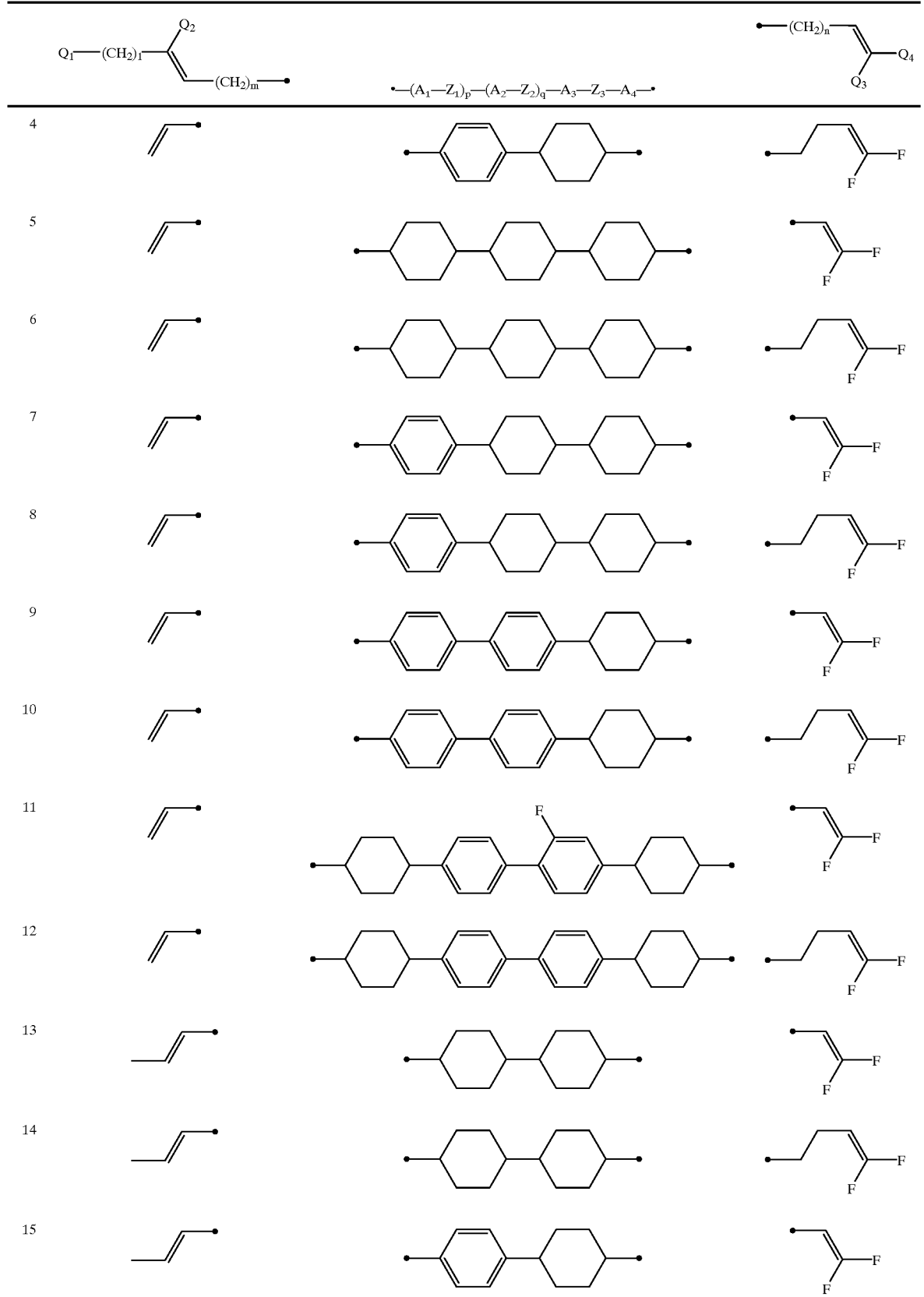

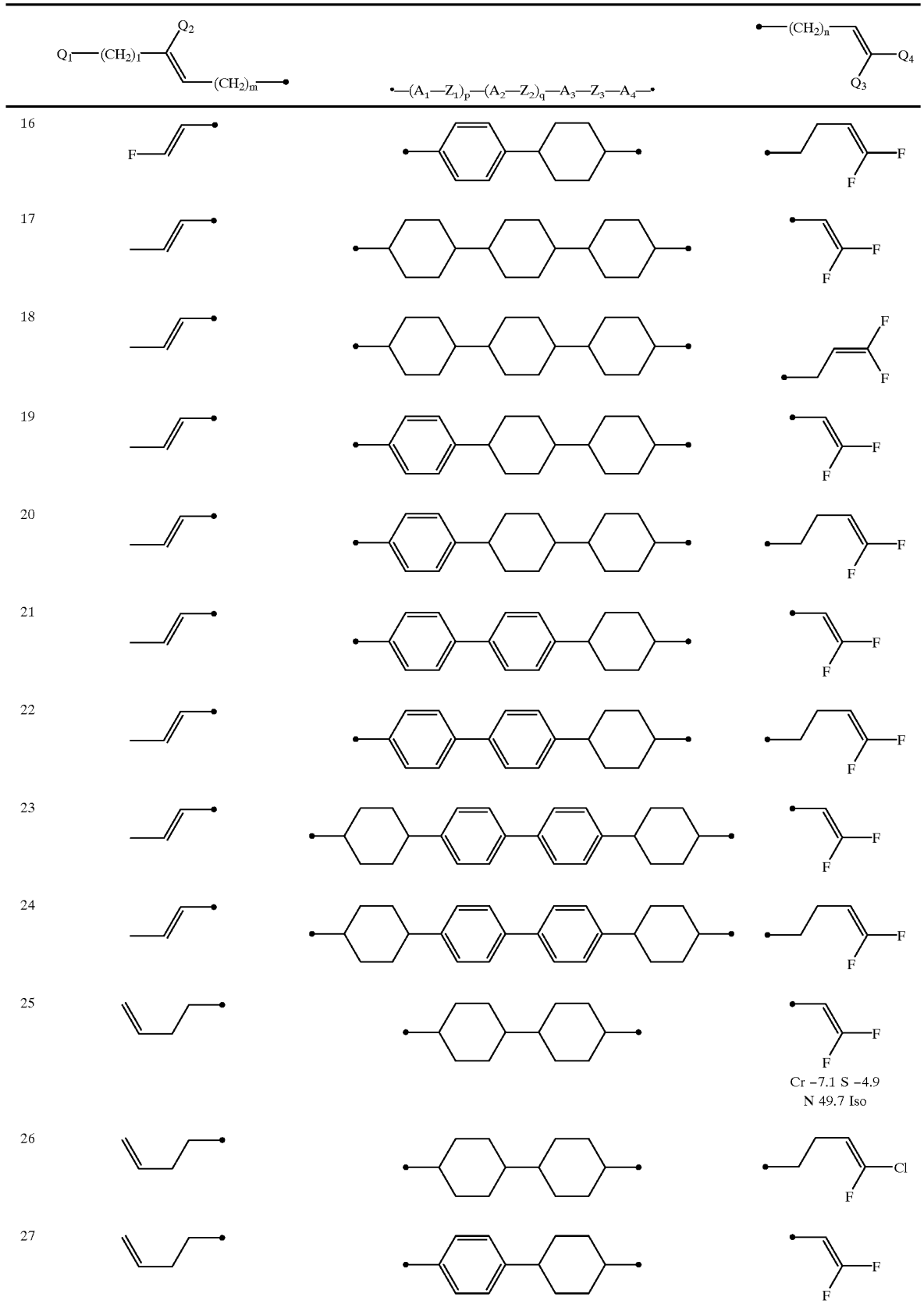

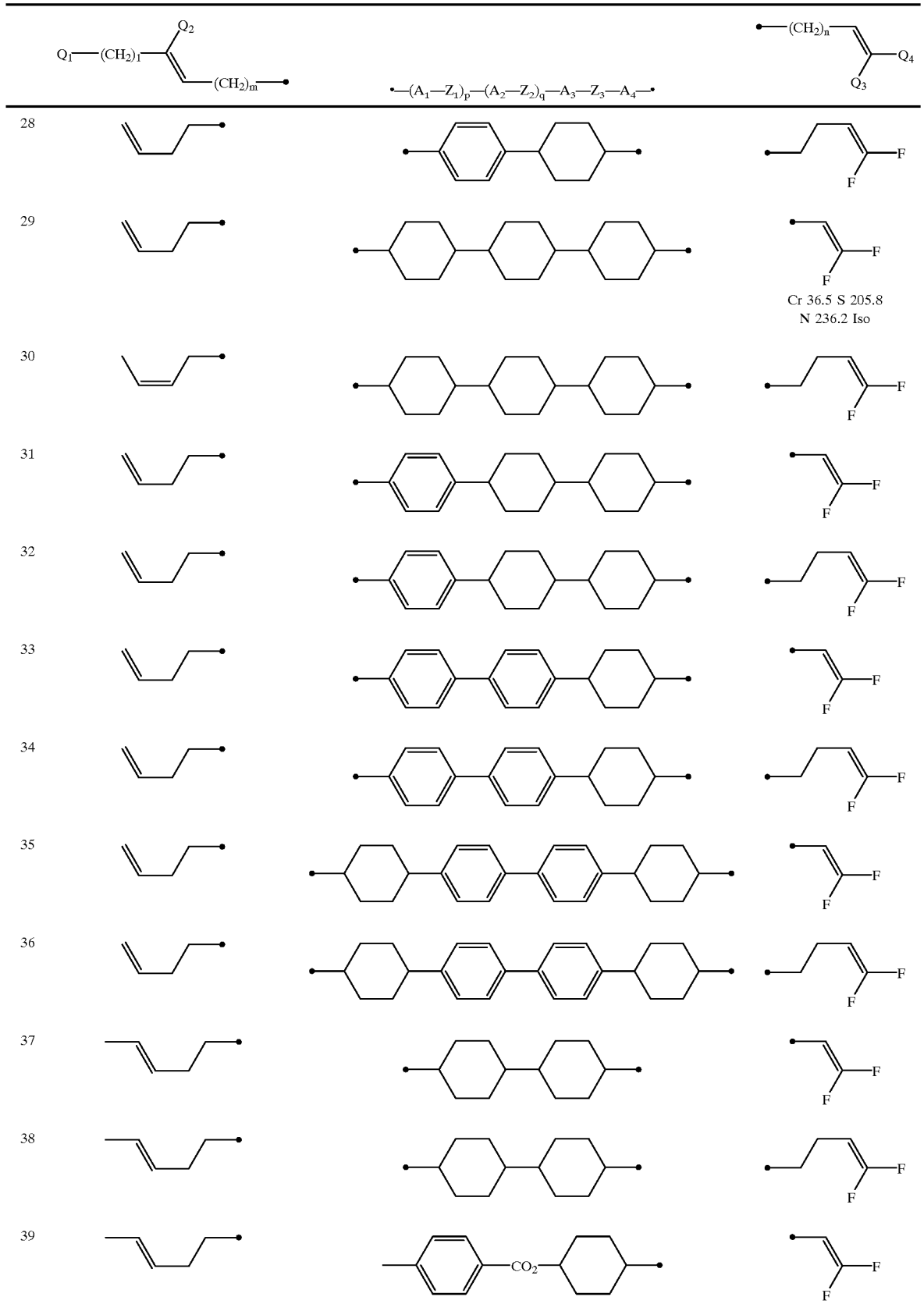

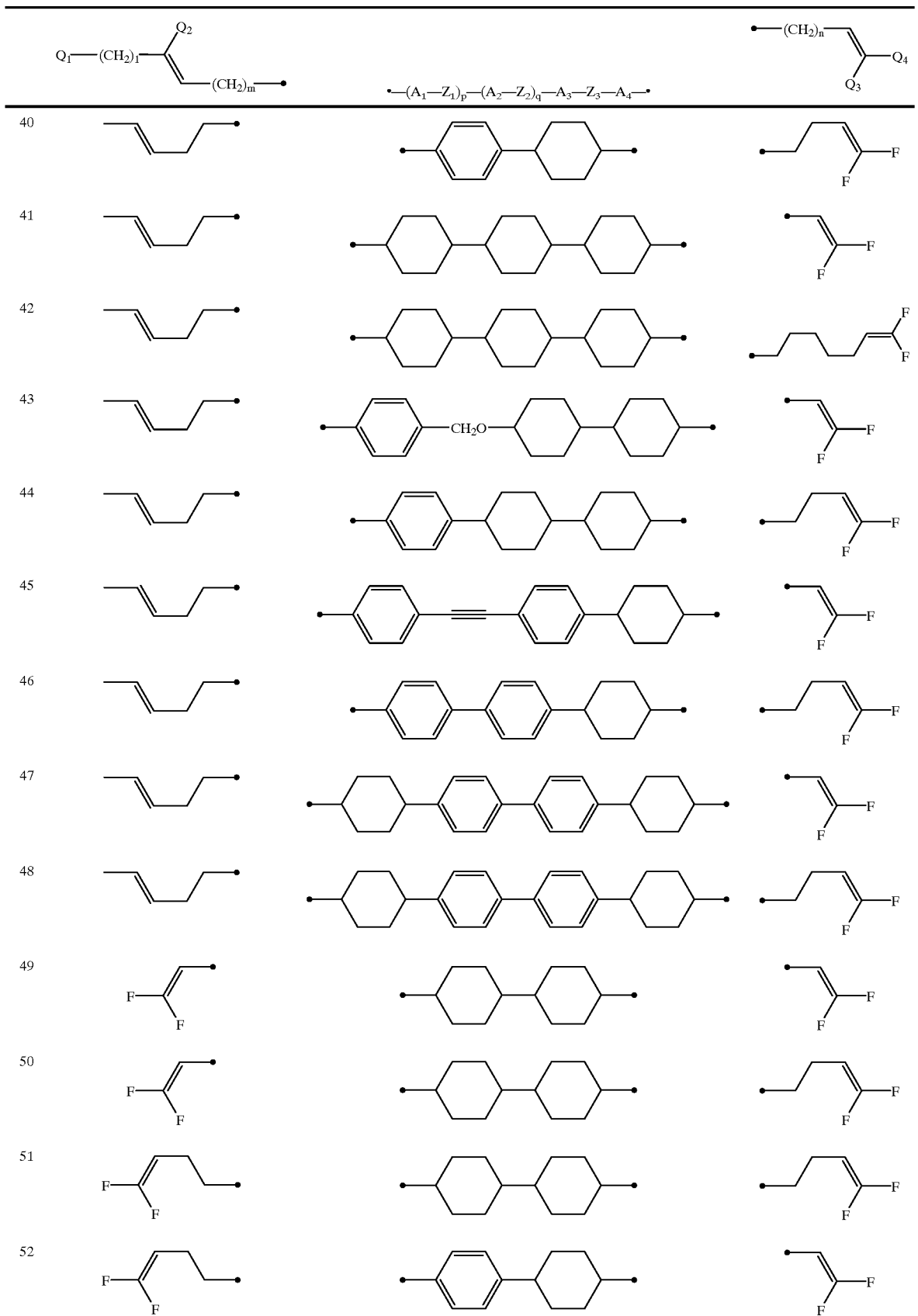

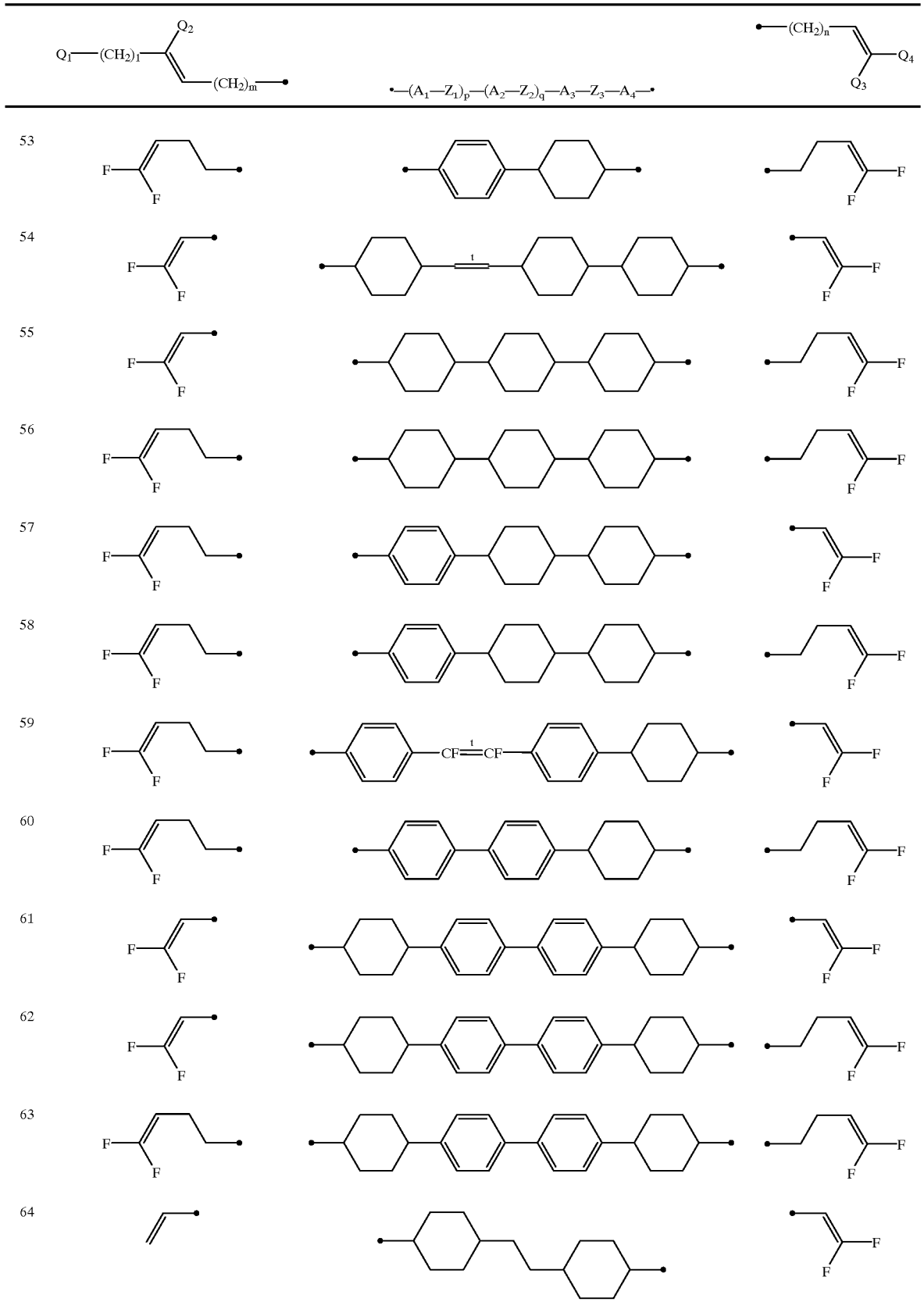

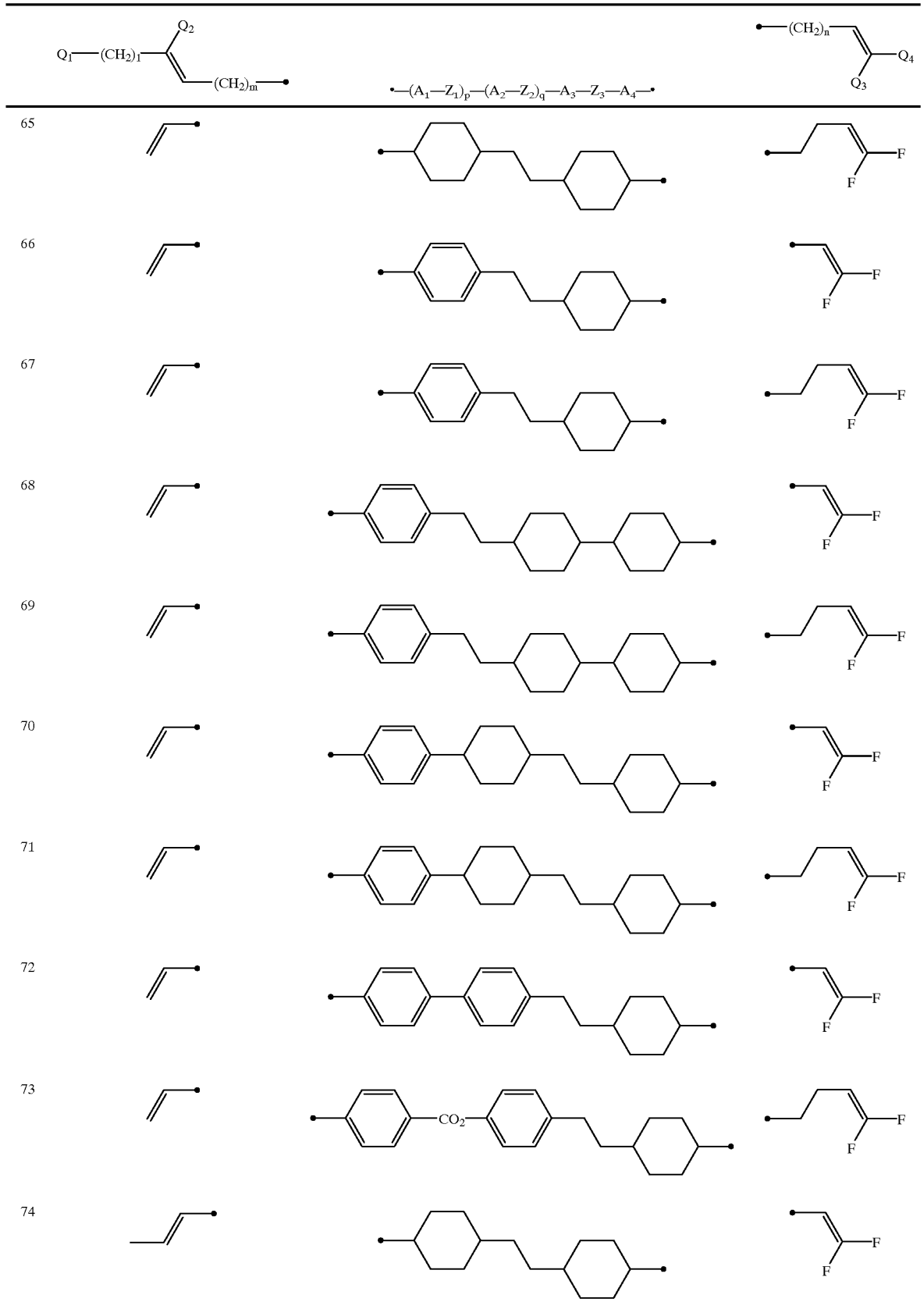

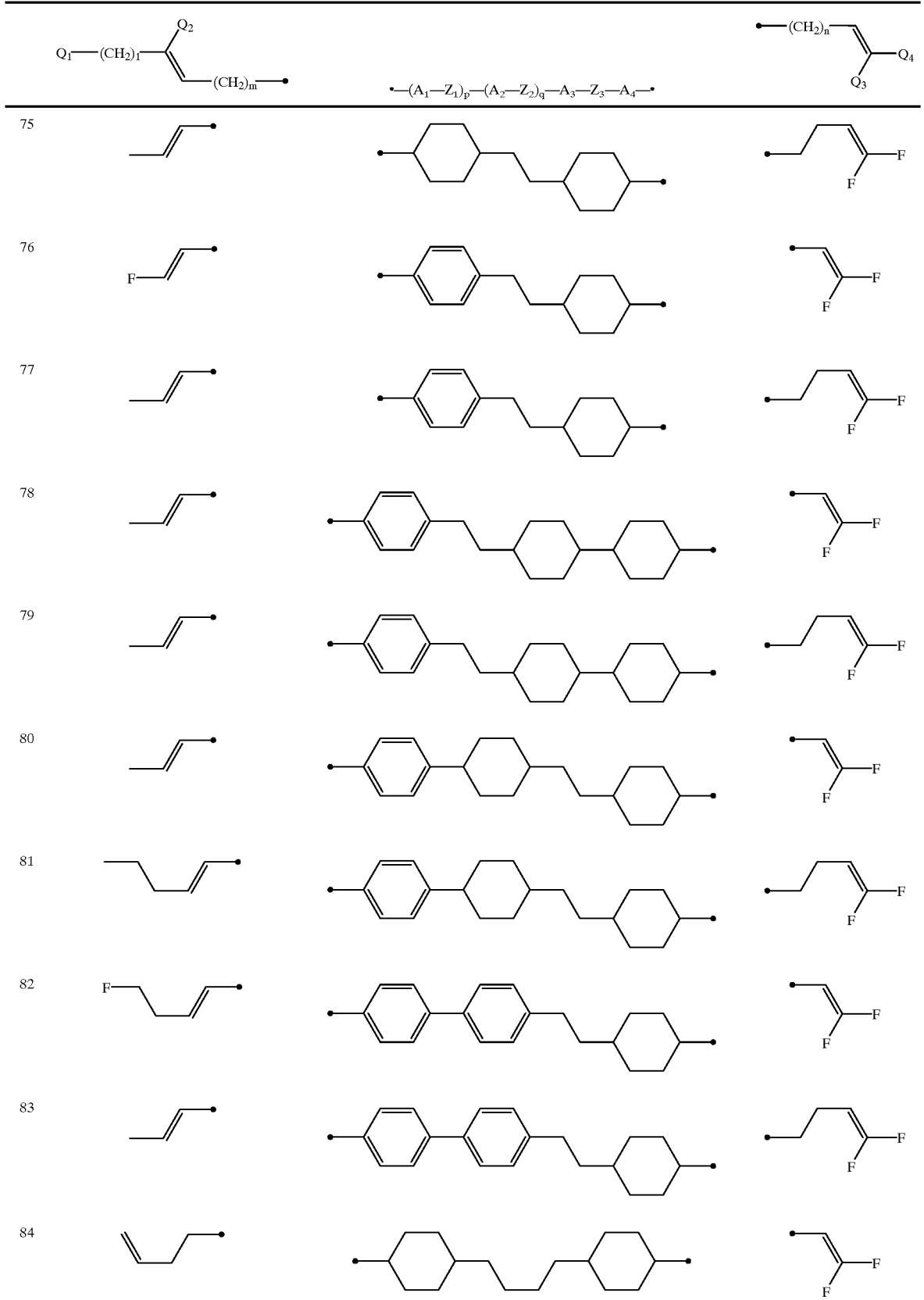

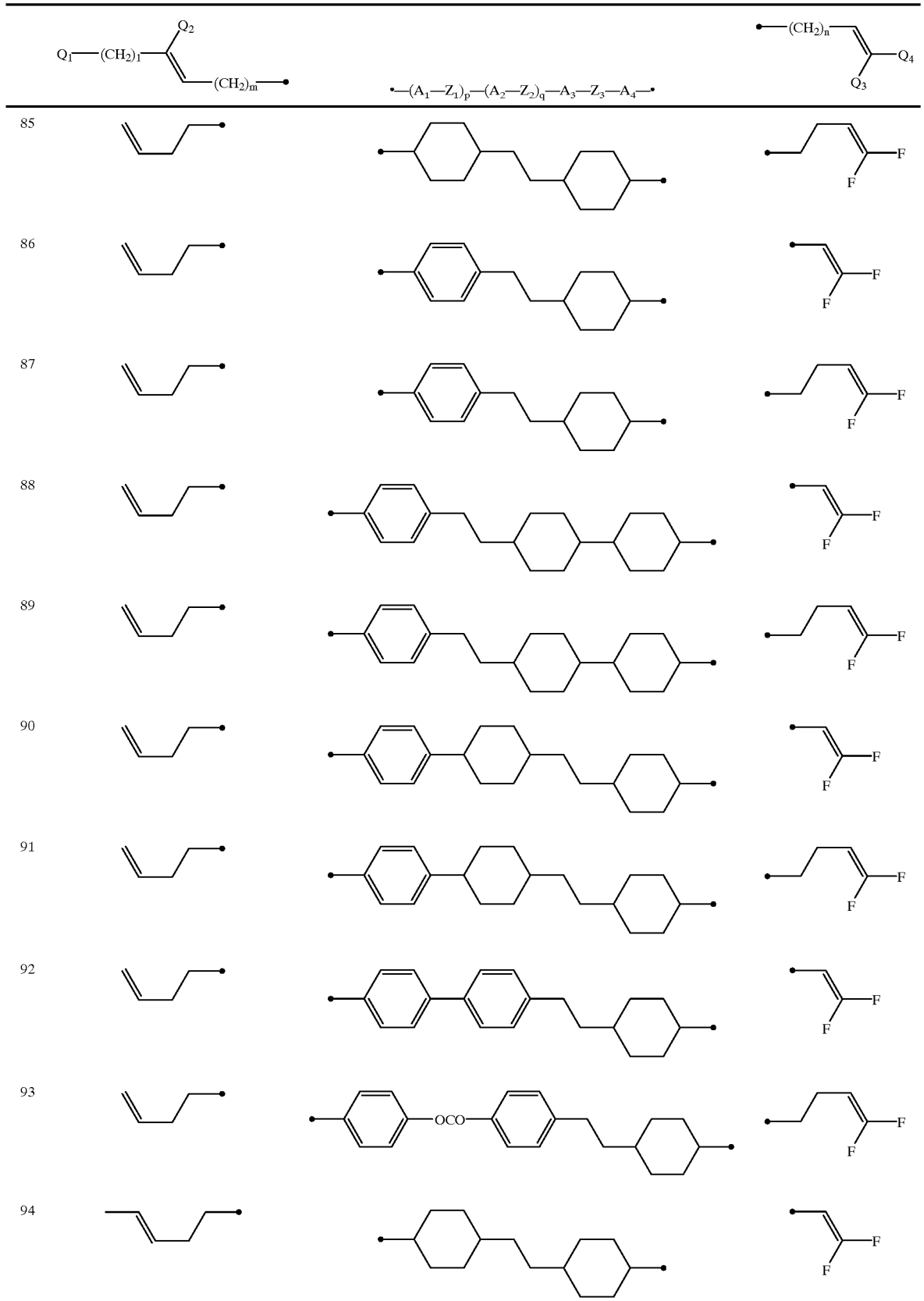

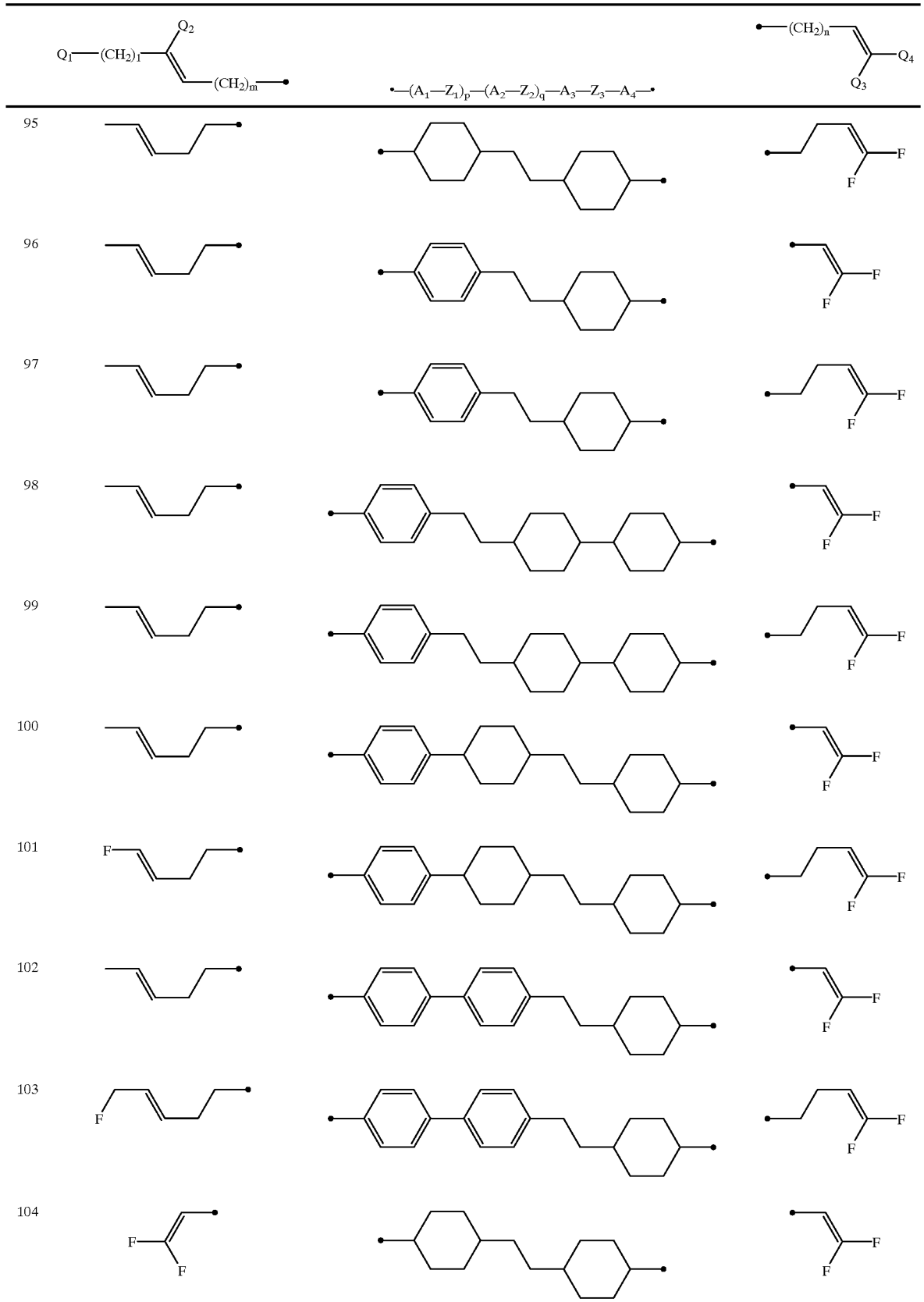

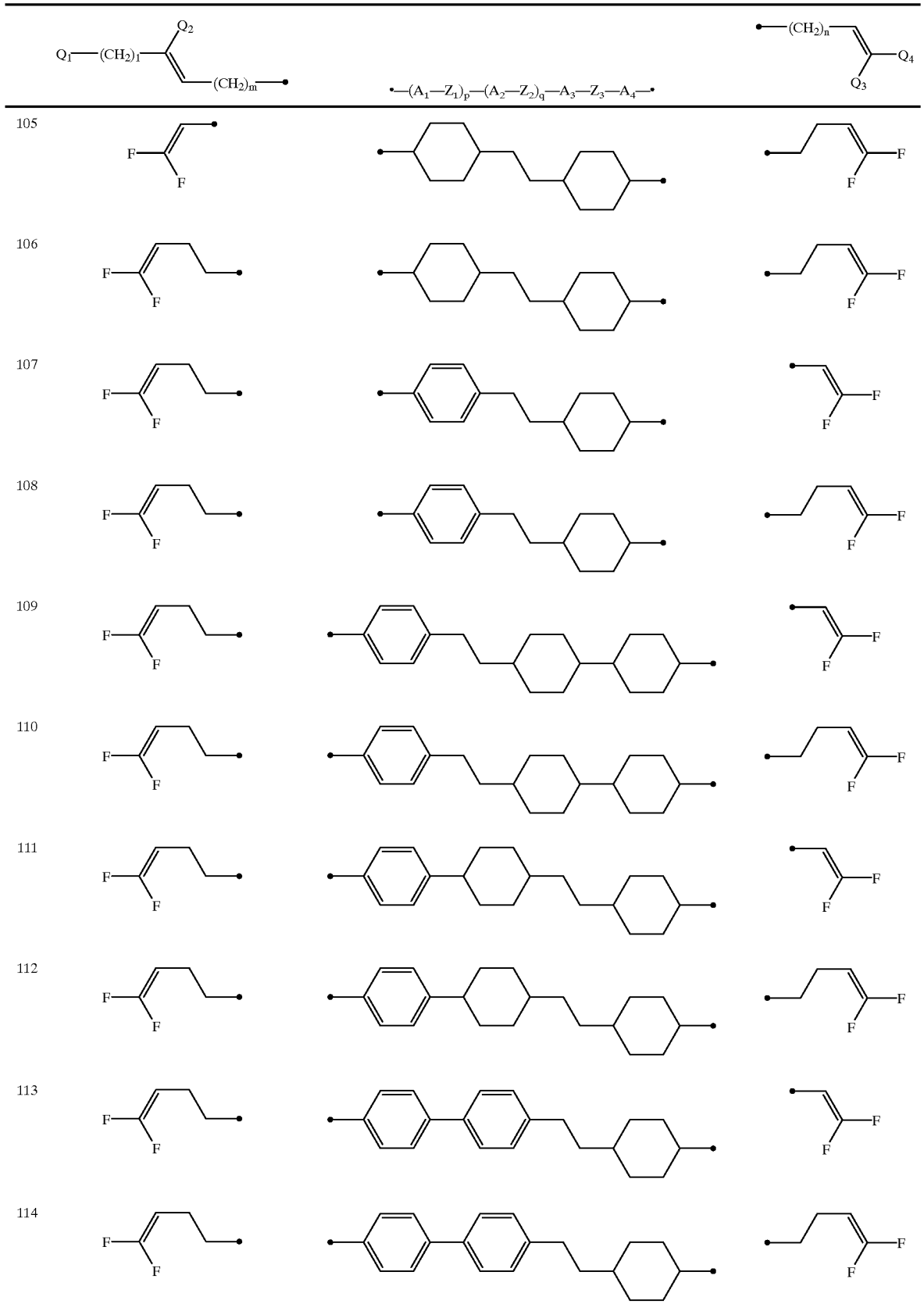

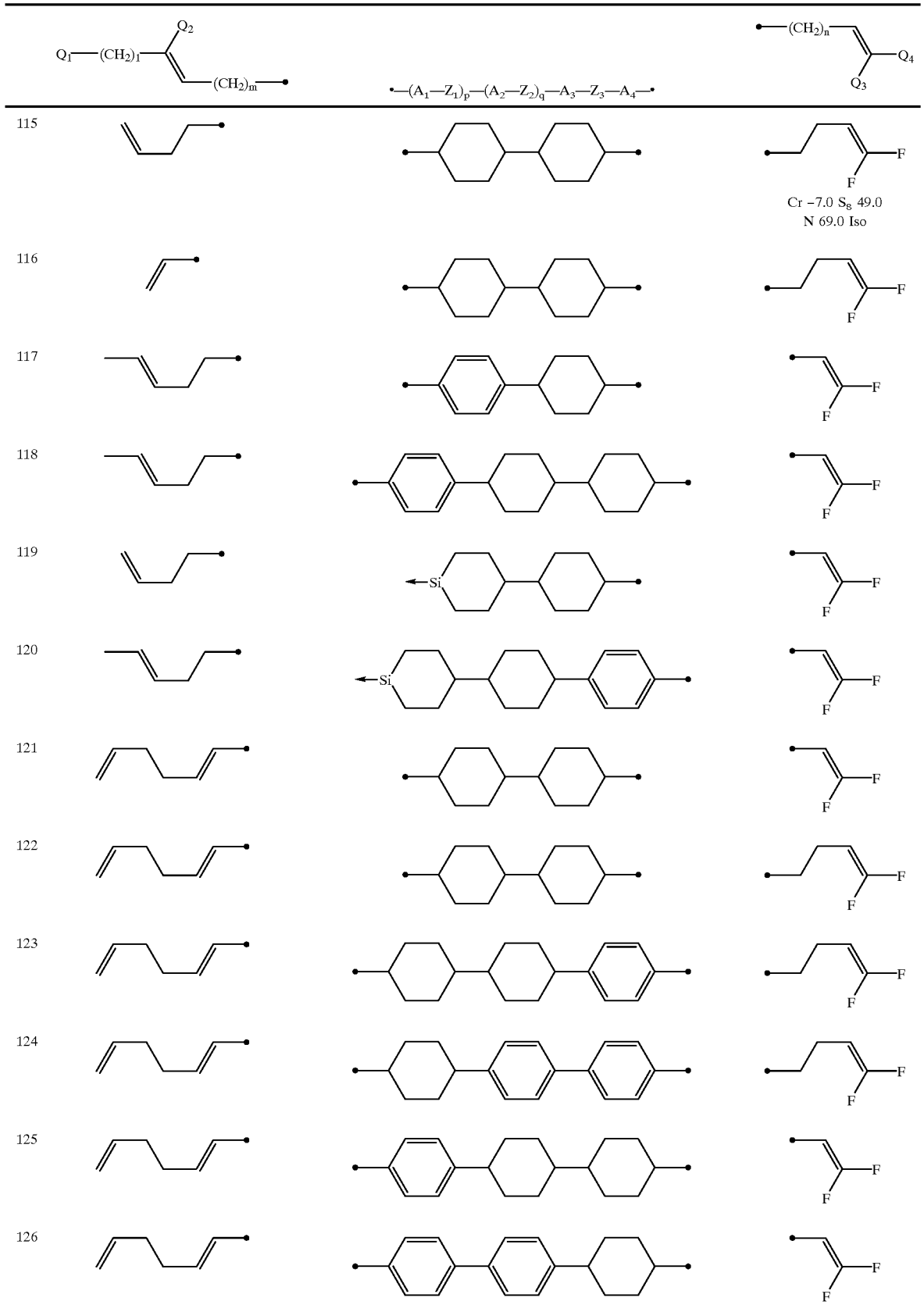

-continued

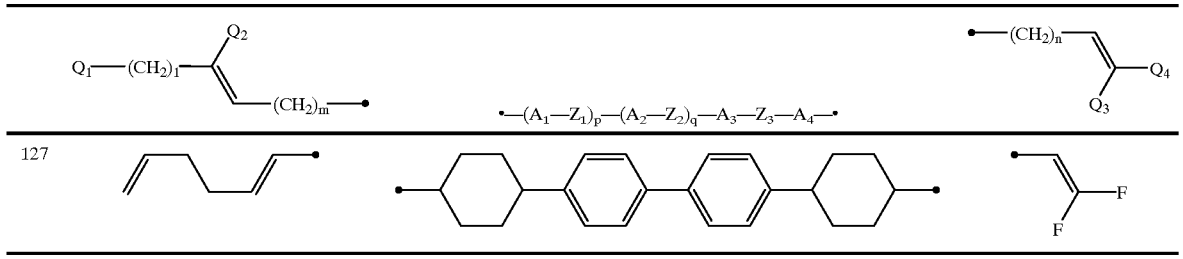

Effects of the Invention

Compounds of the invention, that is, bicyclic to tetracyclic type compounds having an alkenyl group optionally substituted by (a) halogen(s) and an alkenyl group substituted by (a) halogen(s) simultaneously at both terminals of molecule show the following characteristics:

1) They have a wide liquid crystal Phase temperature range in spite of containing an alkenyl group. For example, the compound described in Toku-Kai-Hei 1-175947, trans-4-(trans-4-propylcyclohexyl)-1-(2,2-difluoro-1-ethenyl)cyclohexane, has a liquid crystal phase temperature range of about 47° C., wherein a temperature range of SB phase being about 40° C. In contrast to it, the compound of the present invention, 1-(2,2-difluoroethenyl)-trans-4-(trans-4-(3-butenyl)cyclohexyl) cyclohexane, does not make an appearance of SB phase and has a liquid crystal phase temperature range of about 56° C., which being much improved.
2) There are obtained decrease in a threshold voltage and improvement in a response speed due to a low viscosity.
3) Nematic liquid crystal composition can be prepared without any deposition of crystals and any appearance of smectic phase at an extremely low temperature.
4) A high contrast can be obtained due to improvement in an elastic constant ratio $K_{33}/K_{11}$. As well as, they are stable against external enveironments and also they can provide novel liquid crystal compositions and liquid crystal display devices by which enlargement of the used temperature range, a driving property at a low voltage, a high speed response and a high contrast can be realized.

What is claimed is:

1. A liquid crystalline compound expressed by the general formula (1)

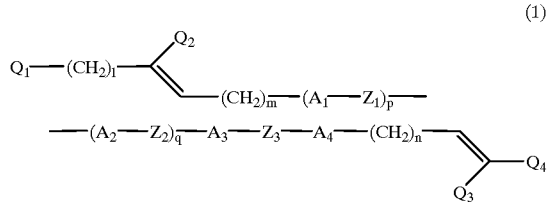

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionally substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently $-(CH_2)_2-$, $-(CH_2)_4-$, $-CH=CH-$, $-COO-$, $-OCO-$, $-CH_2O-$, $OCH_2-$, $-CF=CF-$ or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br and one of $Q_1$, $Q_2$, $Q_3$ and $Q_4$ indispensably denotes F; 1, m and n denote each independently an integer of 0 to 5; and p and q denote each independently an integer of 0 or 1.

2. A liquid crystalline compound according to claim 1, wherein p, q and n are 0; $Q_3$ and $Q_4$ are F; $Z_3$ is a covalent bond; and $A_3$ and $A_4$ are trans-1,4-cyclohexylene groups in the general formula (1).

3. A liquid crystalline compound according to claim 1, wherein p and q are 0; $Q_3$ and $Q_4$ are F; $Z_3$ is a covalent bond; and $A_3$ and $A_4$ are trans-1,4-cyclohexylene groups in the general formula (1).

4. A liquid crystalline compound according to claim 1, wherein p and n are 0; q is 1; $Q_3$ and $Q_4$ are F; $Z_2$ and $Z_3$ are covalent bonds; and $A_2$, $A_3$ and $A_4$ are trans-1,4-cyclohexylene groups in the general formula (1).

5. A liquid crystalline compound according to claim 1, wherein p is 0; q is 1; $Q_3$ and $Q_4$ are F; $Z_2$ and $Z_3$ are covalent bonds; and $A_2$, $A_3$ and $A_4$ are trans-1,4-cyclohexylene groups in the general formula (1).

6. A liquid crystalline compound according to claim 1, wherein p and n are 0; q is 1; $Q_3$ and $Q_4$ are F; $Z_2$ and $Z_3$ are covalent bonds; $A_2$ is 1, 4-phenylene group; and $A_3$ and $A_4$ are trans-1,4-cyclohexylene groups in the general formula (1).

7. A liquid crystalline compound according to claim 1, wherein p is 0; q is 1; $Q_3$ and $Q_4$ are F; $Z_2$ and $Z_3$ are covalent bonds; $A_2$ is 1, 4-phenylene group; and $A_3$ and $A_4$ are trans-1,4-cyclohexylene groups in the general formula (1).

8. A liquid crystalline compound according to claim 1, wherein p and n are 0; q is 1; $Q_3$ and $Q_4$ are F; $Z_2$ and $Z_3$ are covalent bonds; $A_2$ and $A_3$ are 1, 4-phenylene groups, and $A_4$ is trans-1,4-cyclohexylene group in the general formula (1).

9. A liquid crystalline compound according to claim 1, wherein p is 0; q is 1; $Q_3$ and $Q_4$ are F; $Z_2$ and $Z_3$ are covalent bonds; $A_2$ and $A_3$ are 1, 4-phenylene groups; and $A_4$ is trans-1,4-cyclohexylene group in the general formula (1).

10. A liquid crystalline compound according to claim 1, wherein p and q are 1; n is 0; $Q_3$ and $Q_4$ are F; $Z_1$, $Z_2$ and $Z_3$ are covalent bonds; $A_1$ and $A_4$ are trans-1,4-cyclohexylene groups; and $A_2$ and $A_3$ are 1,4-phenylene groups in the general formula (1).

11. A liquid crystalline compound according to claim 1, wherein p and q are 1; $Q_3$ and $Q_4$ are F; $Z_1$, $Z_2$ and $Z_3$ are covalent bonds; $A_1$ and $A_4$ are trans-1,4-cyclohexylene groups, and $A_2$ and $A_3$ are 1, 4-phenylene groups in the general formula (1).

12. A liquid crystal composition consisting of two or more than two components wherein at least one liquid crystal compound(s) according to any one of claims 1–11 is (are) contained.

13. A liquid crystal display device comprising a liquid crystal composition consisting of two or more than two components wherein at least one liquid crystal compound(s) according to any one of claims 1–11 is (are) contained in the composition.

14. A liquid crystal composition comprising at least one liquid crystalline compound(s) expressed by the general formula (1)

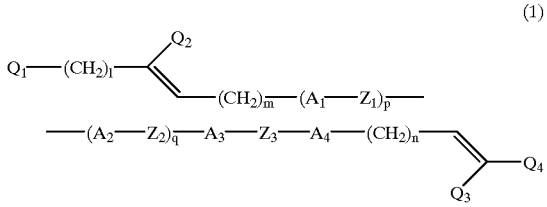

(1)

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —$(CH_2)_2$—, —$(CH_2)_4$—, —CH=CH—, —C≡C—, —COO—, —OCO—, —$CH_2O$—, —$OCH_2$—, —CF=CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, as first component, and at least one compound(s) selected from the group consisting of the general formulae (5), (6), (7), (8) and (9)

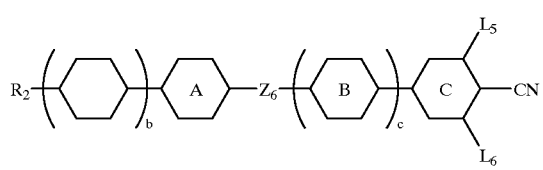

(5)

wherein, $R_2$ denotes F, an alkyl group having 1 to 10 carbon atoms or an alkenyl group having 2 to 10 carbon atoms, in which optional methylene group(s) (—$CH_2$—) in the said alkyl group or alkenyl group may be substituted with (an) oxygen atom(s) (—O—) but two or more than two methylene groups may not be substituted with oxygen atoms consecutively; ring A denotes trans-1,4-cyclohexylene group, 1,4-phenylene group, pyrimidine-2,5-diyl group or 1,3-dioxane-2,5-diyl group; ring B denotes trans-1,4-cyclohexylene group, 1,4-phenylene group or pyrimidine-2, 5-diyl group; ring C denotes trans-1,4-cyclohexylene group or 1,4-phenylene group; $Z_6$ denotes —$(CH_2)_2$—, —COO— or a covalent bond; $L_5$ and $L_6$ denote each independently H or F; and b and c denote each independently 0 or 1,

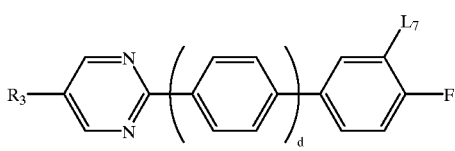

(6)

wherein, $R_3$ denotes an alkyl group having 1 to 10 carbon atoms; $L_7$ denotes H or F; and d denotes 0 or 1,

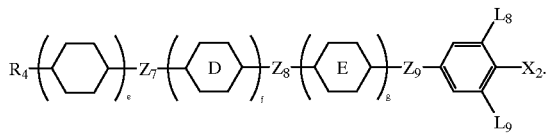

(7)

wherein, $R_4$ denotes an alkyl group having 1 to 10 carbon atoms; ring D and ring E denote each independently trans-1,4-cyclohexylene group or 1,4-phenylene group; $Z_7$ and $Z_8$ denote each independently —COO— or a covalent bond; $Z_9$ denotes —COO— or —C≡C—; $L_8$ and $L_9$ denote each independently H or F; $X_2$ denotes F, $OCF_3$, $OCF_2H$, $CF_3$, $CF_2H$ or $CFH_2$; and e, f and g denote each independently 0 or 1,

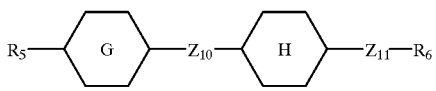

(8)

wherein, $R_5$ and $R_6$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring G denotes trans-1,4-cyclohexylene group, 1,4-phenylene group or pyrimidine-2,5-diyl group; ring H denotes trans-1,4-cyclohexylene group or 1,4-phenylene group; $Z_{10}$ denotes —C≡C—, —COO—, —$(CH_2)_2$—, —CH=CH—C≡C— or a covalent bond; and $Z_{11}$ denotes —COO— or a covalent bond,

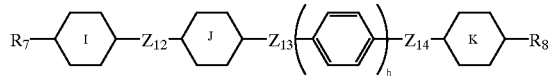

(9)

wherein, $R_7$ and $R_8$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two iethylene groups may not be substituted with oxygen atoms consecutively; ring I denotes trans-1,4-cyclohexylene group, 1,4-phenylene group or pyrimidine-2,5-diyl group; ring J denotes trans-1,4-cyclohexylene group, 1,4-phenylene group in which one or more than one hydrogen atom(s) on ring may be substituted with F, or pyrimidine-2,5-diyl group; ring K denotes trans-1,4-cyclohexylene group or 1,4-phenylene group; $Z_{12}$ and $Z_{14}$ denote each independently —COO—, —(CH$_2$)$_2$— or a covalent bond; $Z_{13}$ denotes —CH═CH—, —C≡C—, —COO— or a covalent bond; and h denotes 0 or 1, is (are) contained as the second component.

15. A liquid crystal composition comprising at least one liquid crystalline compound(s) expressed by the general formula (1)

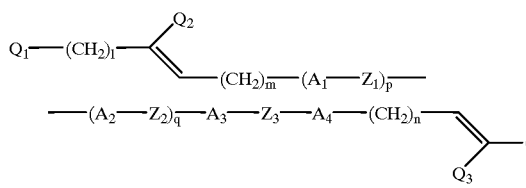

(1)

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —(CH$_2$)$_2$—, —(CH$_2$)$_4$—, —CH═CH—, —C≡C—, —COO—, —OCO—, —CH$_2$O—, —OCH$_2$—, —CF═CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, as a first component, and at least one compound(s) selected from the group consisting of the general formulae (2), (3) and (4)

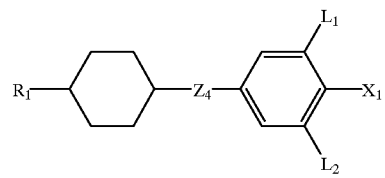

(2)

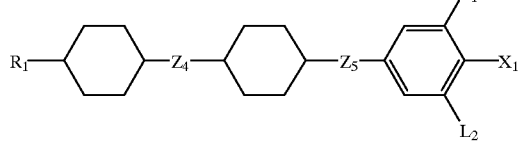

(3)

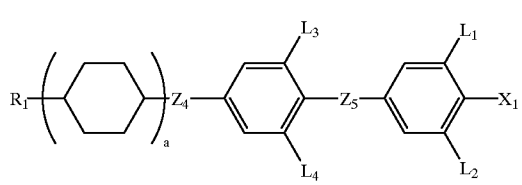

(4)

wherein, $R_1$ denotes an alkyl group having 1 to 10 carbon atoms; $X_1$ denotes F, Cl, OCF$_3$, OCF$_2$H, CF$_3$, CF$_2$H or CFH$_2$; $L_1$, $L_2$, $L_3$ and $L_4$ denote each independently H or F; $Z_4$ and $Z_5$ denote each independently —(CH$_2$)$_2$—, —CH═CH— or a covalent bond; and a denotes 1 or 2, as second component.

16. A liquid crystal composition comprising at least one liquid crystalline compound(s) expressed by the general formula (1)

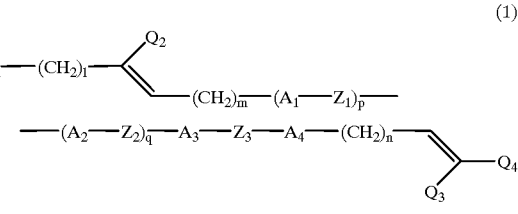

(1)

wherein, $A_1$, $A_2$, $A_3$ and $A_4$ denote each independently trans-1,4-cyclohexylene group, trans-1,4-silacyclohexylene group, 1,4-phenylene group in which one or more than one hydrogen atom(s) on 6-membered ring(s) are optionaly substituted with (a) halogen atom(s), pyrimidine-2,5-diyl group, 1,3-dioxane-2,5-diyl group, tetrahydropyran-2,5-diyl group, 1,3-dithiane-2,5-diyl group or tetrahydrothiopyran-2,5-diyl group; $Z_1$, $Z_2$ and $Z_3$ denote each independently —(CH$_2$)$_2$—, —(CH$_2$)$_4$—, —CH═CH—, —C≡C—, —COO—, —OCO—, —CH$_2$O—, —OCH$_2$—, —CF═CF— or a covalent bond; $Q_1$ and $Q_2$ denote each independently H, F, Cl, Br or an alkenyl group having 2 to 5 carbon atoms; $Q_3$ and $Q_4$ denote each independently H, F, Cl or Br; l, m and n denote each independently an integer of 0 to 5; and p and q denote each independently an integer of 0 or 1, as a first component, at least one compound(s) selected from the group consisting of the general formulae (2), (3) and (4)

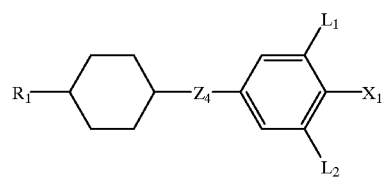

(2)

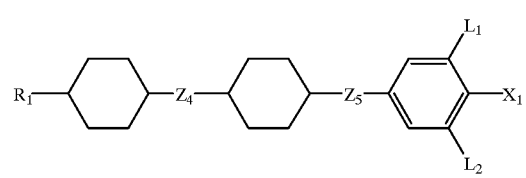

(3)

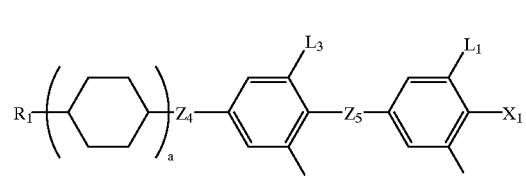

(4)

wherein, $R_1$ denotes an alkyl group having 1 to 10 carbon atoms; $X_1$ denotes F, Cl, OCF$_3$, OCF$_2$H, CF$_3$, CF$_2$H or CFH$_2$; $L_1$, $L_2$, $L_3$ and $L_4$ denote each independently H or F; $Z_4$ and $Z_5$ denote each independently —(CH$_2$)$_2$—, —CH═CH— or a covalent bond; and a denotes 1 or 2, as one part of a second component, and at least one compound (s) selected from the group consisting of the general formulae (5), (6), (7), (8) and (9)

(5)

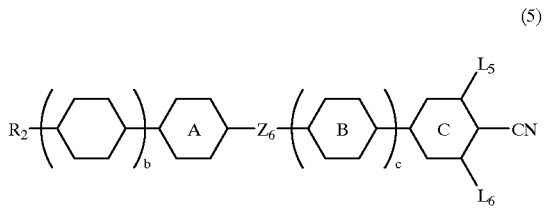

wherein, $R_2$ denotes F, an alkyl group having 1 to 10 carbon atoms or an alkenyl group having 2 to 10 carbon atoms, in which optional methylene group(s) (—$CH_2$—) in the said alkyl group or alkenyl group may be substituted with (an) oxygen atom(s) (—O—) out two or more than two methylene groups may not be substituted with oxygen atoms consecutively; ring A denotes trans-1,4-cyclohexylene group, 1,4-phenylene group, pyrimidine-2,5-diyl group or 1,3-dioxane-2,5-diyl group; ring B denotes trans-1,4-cyclohexylene group, 1,4-phenylene group or pyrimidine-2,5-diyl group; ring C denotes trans-1,4-cyclohexylene group or 1,4-henylene group; $Z_6$ denotes —($CH_2$)$_2$—, —COO— or a covalent bond; $L_5$ and $L_6$ denote each independently H or F; and b and c denote each independently 0 or 1, (6)

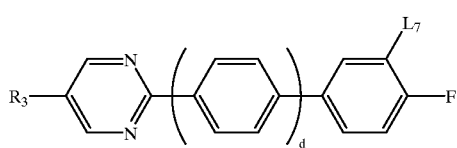

wherein, $R_3$ denotes an alkyl group having 1 to 10 carbon atoms; $L_7$ denotes H or F; and d denotes 0 or 1, (7)

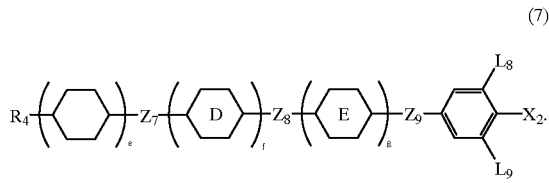

wherein, $R_4$ denotes an alkyl group having 1 to 10 carbon atoms; ring D and ring E denote each independently trans-1,4-cyclohexylene group or 1,4-phenylene group; $Z_7$ and $Z_8$ denote each independently —COO— or a covalent bond; $Z_9$ denotes —COO— or —C≡C—; $L_8$ and $L_9$ denote each independently H or F; $X_2$ denotes F, $OCF_3$, $OCF_2H$, $CF_3$, $CF_2H$ or $CFH_2$; and e, f and g denote each independently 0 or 1, (8)

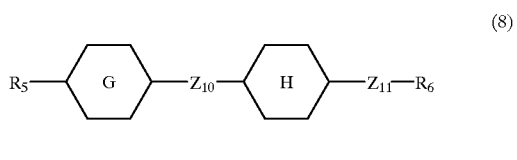

wherein, $R_5$ and $R_6$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring G denotes trans-1,4-cyclohexylene group, 1,4-phenylene group or pyrimidine-2,5-diyl group; ring H denotes trans-1,4-cyclohexylene group or 1,4-phenylene group; $Z_{10}$ denotes —C≡C—, —COO—, —($CH_2$)$_2$—, —CH═CH—C≡C— or a covalent bond; and $Z_{11}$ denotes —COO— or a covalent bond, (9)

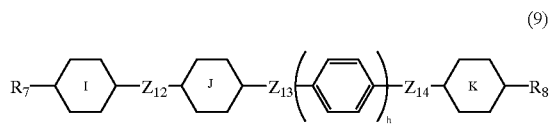

wherein, $R_7$ and $R_8$ denote each independently an alkyl group having 1 to 10 carbon atom(s) or an alkenyl group having 2 to 10 carbon atoms, in which optional methylene group(s) (—$CH_2$—) in either cases may be substituted with (an) oxygen atom(s) (—O—) but two or more than two methylene groups may not be substituted with oxygen atoms consecutively; ring I denotes trans-1,4-cyclohexylene group, 1,4-phenylene group or pyrimidine-2,5-diyl group; ring J denotes trans-1,4-cyclohexylene group, 1,4-phenylene group in which one or more than one hydrogen atom(s) on ring may be substituted with F, or pyrimidine-2,5-diyl group; ring K denotes trans-1,4-cyclohexylene group or 1,4-phenylene group; $Z_{12}$ and $Z_{14}$ denote each independently —COO—, —($CH_2$)$_2$— or a covalent bond; $Z_{13}$ denotes —CH═CH—, —C≡C—, —COO— or a covalent bond; and h denotes 0 or 1, as remainder of the second component.

17. A liquid crystal display device comprising the liquid crystal composition of claim 16.

* * * * *